(12) United States Patent
Matsumoto et al.

(10) Patent No.: US 7,026,094 B2
(45) Date of Patent: Apr. 11, 2006

(54) SUBSTITUTED OXIME DERIVATIVES AND THE USE THEREOF AS LATENT ACIDS

(75) Inventors: Akira Matsumoto, Basel (CH); Hitoshi Yamato, Takarazuka (JP); Toshikage Asakura, Minoo (JP); Masaki Ohwa, Kobe (JP); Peter Murer, Allschwil (CH)

(73) Assignee: Ciba Specialty Chemicals Corp., Tarrytown, NY (US)

( * ) Notice: Subject to any disclaimer, the term of this patent is extended or adjusted under 35 U.S.C. 154(b) by 276 days.

(21) Appl. No.: 10/478,963

(22) PCT Filed: May 23, 2002

(86) PCT No.: PCT/EP02/05667

§ 371 (c)(1),
(2), (4) Date: Nov. 26, 2003

(87) PCT Pub. No.: WO02/098870

PCT Pub. Date: Dec. 12, 2002

(65) Prior Publication Data

US 2004/0209186 A1 Oct. 21, 2004

(30) Foreign Application Priority Data

Jun. 1, 2001 (EP) ............................................. 01810533

(51) Int. Cl.
*G03C 1/494* (2006.01)
*G03C 1/76* (2006.01)

(52) U.S. Cl. ................. 430/270.1; 430/281.1; 430/913; 430/916; 430/919; 430/921; 546/294; 548/556; 549/68; 549/75; 558/408; 564/253

(58) Field of Classification Search .............. 430/270.1, 430/281.1, 913, 916, 919, 921; 564/253; 549/68, 75; 558/408; 546/294; 548/556
See application file for complete search history.

(56) References Cited

U.S. PATENT DOCUMENTS

| 4,540,598 A | 9/1985 | Berner et al. ............... 427/54.1 |
| 4,736,055 A | 4/1988 | Dietliker et al. ............... 560/13 |

(Continued)

FOREIGN PATENT DOCUMENTS

| EP | 0241423 | 10/1987 |
| GB | 2306958 | 5/1997 |

(Continued)

OTHER PUBLICATIONS

Derwent Abstract 87–286243/41 for EP 0241423 (1987).
A. Toshikage et al., Journal of Photopolymer Science and Technology, vol. 13, No. 2, (2000), pp. 223–230.
W. J. Mijs et al., Journal of Coatings Technology, vol. 55, No. 697, (1983), pp. 45–51.

*Primary Examiner*—Yvette C. Thornton
(74) *Attorney, Agent, or Firm*—Tyler A. Stevenson

(57) ABSTRACT

New oxime sulfonate compounds of the formula (I) and (II), wherein $R_1$ is $C_1$–$C_{12}$alkyl, $C_1C_4$haloalkyl, hydrogen, $OR_9$, $NR_{10}R_{11}$, $SR_{12}$ or is phenyl which is unsubstituted or substituted by OH, $C_1$–$C_{18}$alkyl, halogen and/or $C_1$–$C_{12}$alkoxy; $R_2$, $R_3$, $R_4$ and $R_5$ are for example hydrogen or $C_1$–$C_{12}$alkyl; $R_6$ is for example is $C_1$–$C_{18}$alkylsulfonyl, phenyl-$C_1$–$C_3$alkylsulfonyl or phenylsulfonyl; $R'_6$ is for example phenylenedisulfonyl or diphenylenedisulfonyl; $R_7$, $R_8$ and $R_9$ for example are hydrogen or $C_1$–$C_6$alkyl; $R_{10}$ and $R_{11}$, are for example hydrogen or $C_1$–$C_{18}$alkyl; $R_{12}$ is for example hydrogen, phenyl or $C_1$–$C_{18}$alkyl; A is S, O, $NR_{13}$, or a group of formula A1, A2 or A3, $R_{21}$ and R22 independently of one other have one of the meanings given for $R_7$; $R_{23}$, $R_{24}$, $R_{25}$ and $R_{26}$ independently of one another are for example hydrogen, $C_1$–$C_4$alkyl, halogen or phenyl; Z is $CR_{22}$ or N; and $Z_1$ is $CR_{22}$ or N; and $Z_1$ is $CR_{22}$ or N; and $Z_1$ is $CH_2$, S, O or $NR_{13}$ are particularly suitable as photo-latent acids in resist applications.

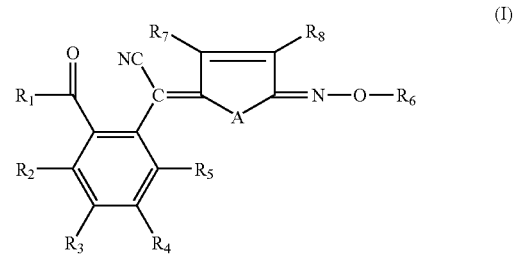

(I)

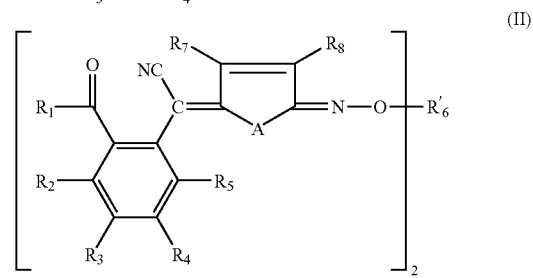

(II)

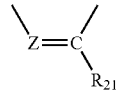

(A₁)

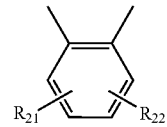

(A₂)

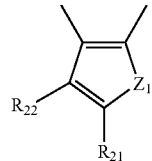

(A₃)

19 Claims, No Drawings

U.S. PATENT DOCUMENTS

| | | | |
|---|---|---|---|
| 5,627,011 A | 5/1997 | Münzel et al. | 430/270.1 |
| 5,714,625 A | 2/1998 | Hada et al. | 558/437 |
| 5,759,740 A | 6/1998 | Münzel et al. | 430/270.1 |
| 6,004,724 A * | 12/1999 | Yamato et al. | 430/281.1 |
| 6,485,886 B1 * | 11/2002 | Yamato et al. | 430/270.1 |
| 6,770,420 B1 * | 8/2004 | Dietliker et al. | 430/270.1 |
| 6,806,024 B1 * | 10/2004 | Kura et al. | 430/270.1 |
| 2004/0002007 A1 | 1/2004 | Hitoshi et al. | 430/1 |

FOREIGN PATENT DOCUMENTS

| | | |
|---|---|---|
| WO | 99/01429 | 1/1999 |
| WO | 00/26219 | 5/2000 |
| WO | 00/52530 | 9/2000 |

* cited by examiner

SUBSTITUTED OXIME DERIVATIVES AND THE USE THEREOF AS LATENT ACIDS

The invention relates to new oxime derivatives, chemically amplified photoresist compositions comprising said compounds and to the use of the compounds as latent acids, which can be activated by irradiation with actinic electromagnetic radiation and electron beams.

In U.S. Pat. No. 4,540,598 surface-coating compositions comprising photosensitive oxime sulfonate compounds, e.g. 4-chloro-α-trifluoroacetophenonoxime benzenesulfonate and customary acid-curable resins are disclosed. In U.S. Pat. No. 4,736,055 2,2,2-trifluoro-1-phenyl-ethanone oxime-O-(4-hydroxyphenylsulfonate) is described as a component for the preparation of polymers which can be used as resins in positive photoresists. In U.S. Pat. No. 5,627,011 and U.S. Pat. No. 5,759,740 the use of α-(4-toluene-sulfonyloxyimino)-4-methoxybenzyl cyanide and α-(4-toluene-sulfonyloxyimino)-3-thienylmethyl cyanide as latent acid catalysts in chemically amplified positive and negative photoresists for wavelengths of 340–390 nm, especially those in the radiation region of the mercury i line (365 nm) is described. In GB 2306958 the use of oxime-sulfonates as latent acid donors in positive and negative photoresists for wavelengths between 180 and 600 nm, especially those in the radiation region beyond 390 nm is reported. In U.S. Pat. No. 5,714,625 non aromatic α-(alkylsulfonyloxyimino)-1-cyclohexenylacetonitriles and α-(alkylsulfonyloxyimino)-1-cyclopentenylacetonitriles are disclosed. In EP 241423 oxime sulfonate compounds are employed in about 25% concentration as photolatent acid generators in non-chemically amplified positive resists. In U.S. Pat. No. 6,004,724, WO 00/26219, and J. Photopolym. Sci. Technol. 13, 223 (2000), oxime derivatives, e.g. (5-methylsulfonyloxyimino-5H-thiophen-2-ylidene)-2-methylphenyl-acetonitrile, are described as photolatent acid generators for the chemically amplified resists. In WO 00/52530, oxime derivatives, e.g. (5-methylsulfonyloxyimino-5H-thiophen-2-ylidene)-2-methylphenyl-acetonitrile, are described as photoinitiator for radical photopolymerization.

In the art exists a need for reactive non-ionic latent acid donors that are thermally and chemically stable and that, after being activated by light, UV-radiation, X-ray irradiation or electron beams can be used as catalysts for a variety of acid-catalysed reactions, such as polycondensation reactions, acid-catalysed depolymerisation reactions, acid-catalysed electrophilic substitution reactions or the acid-catalysed removal of protecting groups. A particular need exists for latent acid catalysts with high stability and good solubility in the field of chemically amplified photoresists.

Surprisingly, it has now been found that specific oxime derivatives, as described below, are especially suitable as catalysts for the aforementioned acid catalyzed reactions. The optical absorption spectra of the specific compounds of the invention are tunable over a wide range of the electromagnetic spectrum and particularly suitable for applications in the deep UV range. Furthermore, chemically amplified photoresist compositions comprising oxime derivatives of the present invention are thermally stable, even at high bake temperatures during processing and provide high photospeed.

The invention accordingly relates to compounds of the formula I or II

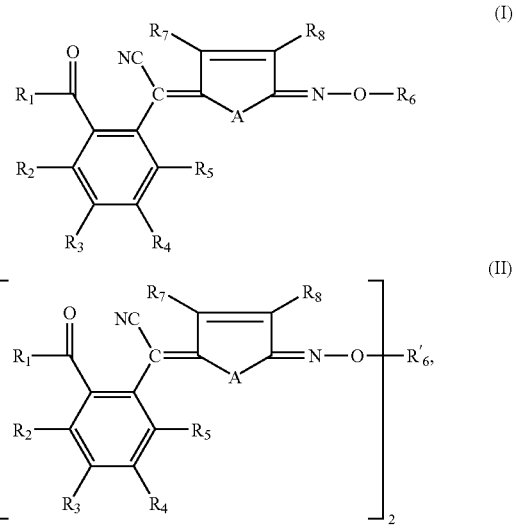

wherein
$R_1$ is $C_1$–$C_{12}$alkyl, $C_1$–$C_4$haloalkyl, hydrogen, $OR_9$, $NR_{10}R_{11}$, $SR_{12}$ or is phenyl which is unsubstituted or substituted by OH, $C_1$–$C_{18}$alkyl, halogen and/or $C_1$–$C_{12}$alkoxy;
$R_2$, $R_3$, $R_4$ and $R_5$ are independently of each other hydrogen, $C_1$–$C_{12}$alkyl, $C_1$–$C_4$haloalkyl, halogen, phenyl, $OR_{13}$, $NR_{14}R_{15}$, $SR_{15}$, CN, $NO_2$, $C_2$–$C_6$alkanoyl, benzoyl, —(CO)$OR_9$, —(CO)$NR_{10}R_{11}$ or —(CO)$SR_{12}$;
$R_6$ is $C_1$–$C_{18}$alkylsulfonyl, $C_1$–$C_{10}$haloalkylsulfonyl, camphorylsulfonyl, phenyl-$C_1$–$C_3$alkylsulfonyl, $C_3$–$C_{30}$cycloalkylsulfonyl, phenylsulfonyl, naphthylsulfonyl, anthracylsulfonyl or phenanthrylsulfonyl, wherein the groups cycloalkyl, phenyl, naphthyl, anthracyl and phenanthryl of the radicals $C_3$–$C_{30}$cycloalkylsulfonyl, phenyl-$C_1$–$C_3$alkylsulfonyl, phenylsulfonyl, naphthylsulfonyl, anthracylsulfonyl and phenanthrylsulfonyl are unsubstituted or substituted by one or more halogen, $C_1$–$C_4$haloalkyl, CN, $NO_2$, $C_1$–$C_{16}$alkyl, phenyl, $C_1$–$C_4$alkylthio, $OR_{13}$, (CO)$OR_9$, $C_1$–$C_4$alkyl-(CO)O—, $R_9OSO_2$— and/or —$NR_{14}R_{15}$; or $R_6$ is $C_2$–$C_6$haloalkanoyl, halobenzoyl; or $R_6$ is a group

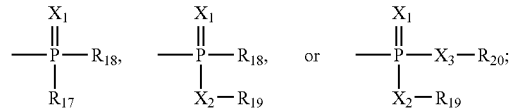

$X_1$, $X_2$ and $X_3$ independently of each other are O or S;
$R'_6$ is phenylenedisulfonyl, naphthylenedisulfonyl,

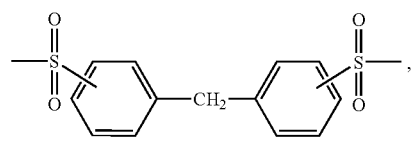

diphenylenedisulfonyl, or oxydiphenylenedisulfonyl, wherein these radicals are unsubstituted or substituted by $C_1$–$C_{12}$alkyl; or $R'_6$ is $C_2$–$C_{12}$alkylenedisulfonyl;
$R_7$ and $R_8$ are independently of each other hydrogen, halogen, $C_1$–$C_6$alkyl, $C_1$–$C_6$alkoxy, $C_1$–$C_4$haloalkyl, CN, $NO_2$, $C_2$–$C_6$alkanoyl, benzoyl, phenyl, —S-phenyl, $OR_{13}$, $SR_{16}$, $NR_{14}R_{15}$, $C_2$–$C_6$alkoxycarbonyl, phenoxycarbonyl, $S(O)_nC_1$–$C_6$alkyl, $S(O)_n$—$C_6$–$C_{12}$aryl, $C_1$–$C_{12}$alkyl-substituted $S(O)_n$–$C_6$–$C_{12}$aryl, $SO_2O$—$C_1$–$C_6$alkyl, $SO_2O$—$C_6$–$C_{10}$aryl or $NHCONH_2$;

n is 0, 1 or 2;

$R_9$ is hydrogen, $C_1$–$C_{18}$alkyl which is unsubstituted or substituted by phenyl, OH, $C_1$–$C_{12}$alkoxy, $C_2$–$C_{12}$alkoxycarbonyl, phenoxy, phenoxycarbonyl, phenylthio, phenylthiocarbonyl, $NR_{14}R_{15}$, $C_1$–$C_{12}$alkylsulfonyl, phenylsulfonyl, (4-methylphenyl)sulfonyl and/or by $C_2$–$C_6$alkanoyl; or $R_9$ is $C_2$–$C_{18}$alkyl which is interrupted by one or more —O—, and which is unsubstituted or substituted by phenyl, OH, $C_1$–$C_{12}$alkoxy, $C_2$–$C_{12}$alkoxycarbonyl, phenoxy, phenoxycarbonyl, phenylthio, phenylthiocarbonyl, $NR_{14}R_{15}$, $C_1$–$C_{12}$alkylsulfonyl, phenylsulfonyl, (4-methylphenyl)sulfonyl and/or by $C_2$–$C_6$alkanoyl; or $R_9$ is phenyl which is unsubstituted or substituted by OH, $C_1$–$C_{18}$alkyl, halogen and/or $C_1$–$C_{12}$alkoxy;

$R_{10}$, $R_{11}$, $R_{14}$ and $R_{15}$ independently of each other are hydrogen or $C_1$–$C_{18}$alkyl which is unsubstituted or substituted by OH, $C_1$–$C_4$alkoxy, $C_2$–$C_{12}$alkoxycarbonyl, phenoxy, phenoxycarbonyl, phenylthio, phenylthiocarbonyl, phenylamino, phenylaminocarbonyl, $C_1$–$C_{12}$alkylsulfonyl, phenylsulfonyl, (4-methyl-phenyl)sulfonyl and/or $C_2$–$C_6$alkanoyl; or $R_{10}$, $R_{11}$, $R_{14}$ and $R_{15}$ are $C_2$–$C_{18}$alkyl which is interrupted by one or more —O—, and which is unsubstituted or substituted by OH, $C_1$–$C_4$alkoxy, $C_2$–$C_{12}$alkoxycarbonyl, phenoxy, phenoxycarbonyl, phenylthio, phenylthiocarbonyl, phenylamino, phenylaminocarbonyl, $C_1$–$C_{12}$alkylsulfonyl, phenylsulfonyl, (4-methylphenyl)sulfonyl and/or $C_2$–$C_6$alkanoyl; or $R_{10}$, $R_{11}$, $R_{14}$ and $R_{15}$ are phenyl which is unsubstituted or substituted by OH, $C_1$–$C_{18}$alkyl, halogen and/or $C_1$–$C_{12}$alkoxy; or $R_{10}$, $R_{11}$, $R_{14}$ and $R_{15}$ are $C_2$–$C_{18}$alkanoyl, which is unsubstituted or substituted by phenyl, OH, $C_1$–$C_{12}$alkoxy, $C_2$–$C_{12}$alkoxycarbonyl, phenoxy, phenoxycarbonyl, phenylthio, phenylthiocarbonyl, phenylamino, phenylaminocarbonyl, $C_1$–$C_{12}$alkylsulfonyl, phenylsulfonyl, (4-methylphenyl)sulfonyl, and/or by $C_2$–$C_6$alkanoyl; or $R_{10}$, $R_{11}$, $R_{14}$ and $R_{15}$ are $C_1$–$C_{18}$alkylsulfonyl which is unsubstituted or substituted by phenyl, OH, $C_1$–$C_{12}$alkoxy, $C_2$–$C_{12}$alkoxycarbonyl, phenoxy, phenoxycarbonyl, phenylthio, phenylthiocarbonyl, phenylamino, phenylaminocarbonyl, $C_1$–$C_{12}$alkylsulfonyl, phenylsulfonyl, (4-methylphenyl)sulfonyl, and/or by $C_2$–$C_6$alkanoyl; or $R_{10}$, $R_{11}$, $R_{14}$ and $R_{15}$ are phenylsulfonyl which is unsubstituted or substituted by one or more halogen, $C_1$–$C_4$haloalkyl, CN, $NO_2$, $C_1$–$C_{16}$alkyl, phenyl, $C_1$–$C_4$alkylthio, $C_1$–$C_{12}$alkoxy and/or phenoxy; or $R_{10}$, $R_{11}$, $R_{14}$ and $R_{15}$ are benzoyl, $C_1$–$C_{10}$haloalkylsulfonyl, camphorylsulfonyl, phenyl-$C_1$–$C_3$alkylsulfonyl, $C_3$–$C_{30}$cycloalkylsulfonyl, naphthylsulfonyl, anthracylsulfonyl or phenanthrylsulfonyl; or $R_{10}$ and $R_{11}$, or $R_{14}$ and $R_{15}$ together with the nitrogen atom to which they are attached, form a 5-, 6- or 7-membered ring which optionally is interrupted by —O— or by —$NR_{13}$—;

$R_{12}$ is hydrogen, phenyl, $C_1$–$C_{18}$alkyl which is unsubstituted or substituted by phenyl, OH, $C_1$–$C_{12}$alkoxy, $C_2$–$C_{12}$alkoxycarbonyl, phenoxy, phenoxycarbonyl, phenylthio, phenylthiocarbonyl, $NR_{14}R_{15}$, $C_1$–$C_{12}$alkylsulfonyl, phenylsulfonyl, (4-methylphenyl)sulfonyl, and/or by $C_2$–$C_6$alkanoyl; or $R_{12}$ is $C_2$–$C_{18}$alkyl which is interrupted by one or more —O— and which is unsubstituted or substituted by phenyl, OH, $C_1$–$C_{12}$alkoxy, $C_2$–$C_{12}$alkoxycarbonyl, phenoxy, phenoxycarbonyl, phenylthio, phenylthiocarbonyl, $NR_{14}R_{15}$, $C_1$–$C_{12}$alkylsulfonyl, phenylsulfonyl, (4-methylphenyl)sulfonyl, and/or by $C_2$–$C_6$alkanoyl;

$R_{13}$ has one of the meanings given for $R_9$ or is $C_2$–$C_{18}$alkanoyl which is unsubstituted or substituted by phenyl, OH, $C_1$–$C_{12}$alkoxy, $C_2$–$C_{12}$alkoxycarbonyl, phenoxy, phenoxycarbonyl, phenylthio, phenylthiocarbonyl, $NR_{14}R_{15}$, $C_1$–$C_{12}$alkylsulfonyl, phenylsulfonyl, (4-methylphenyl)sulfonyl, and/or by $C_2$–$C_6$alkanoyl; or $R_{13}$ is $C_1$–$C_{18}$alkylsulfonyl which is unsubstituted or substituted by phenyl, OH, $C_1$–$C_{12}$alkoxy, $C_2$–$C_{12}$alkoxycarbonyl, phenoxy, phenoxycarbonyl, phenylthio, phenylthiocarbonyl, $NR_{14}R_{15}$, $C_1$–$C_{12}$alkylsulfonyl, phenylsulfonyl, (4-methylphenyl)sulfonyl, and/or by $C_2$–$C_6$alkanoyl; or $R_{13}$ is phenylsulfonyl which is unsubstituted or substituted by one or more halogen, $C_1$–$C_4$haloalkyl, CN, $NO_2$, $C_1$–$C_{16}$alkyl, phenyl, $C_1$–$C_4$alkylthio, $C_1$–$C_{12}$alkoxy and/or phenoxy; or $R_{13}$ is benzoyl, $C_1$–$C_{10}$haloalkylsulfonyl, camphorylsulfonyl, phenyl-$C_1$–$C_3$alkylsulfonyl, $C_3$–$C_{30}$cycloalkylsulfonyl, naphthylsulfonyl, anthracylsulfonyl or phenanthrylsulfonyl;

$R_{16}$ has one of the meanings given for $R_{12}$ or is $C_2$–$C_{18}$alkanoyl which is unsubstituted or substituted by phenyl, OH, $C_1$–$C_{12}$alkoxy, $C_2$–$C_{12}$alkoxycarbonyl, phenoxy, phenoxycarbonyl, phenylthio, phenylthiocarbonyl, $NR_{14}R_{15}$, $C_1$–$C_{12}$alkylsulfonyl, phenylsulfonyl, (4-methylphenyl)sulfonyl, and/or by $C_2$–$C_6$alkanoyl; or $R_{16}$ is $C_1$–$C_{18}$alkylsulfonyl which is unsubstituted or substituted by phenyl, OH, $C_1$–$C_{12}$alkoxy, $C_2$–$C_{12}$alkoxycarbonyl, phenoxy, phenoxycarbonyl, phenylthio, phenylthiocarbonyl, $NR_{14}R_{15}$, $C_1$–$C_{12}$alkylsulfonyl, phenylsulfonyl, (4-methylphenyl)sulfonyl, and/or by $C_2$–$C_6$alkanoyl; or $R_{16}$ is phenylsulfonyl which is unsubstituted or substituted by one or more halogen, $C_1$–$C_4$haloalkyl, CN, $NO_2$, $C_1$–$C_{16}$alkyl, phenyl, $C_1$–$C_4$alkylthio, $C_1$–$C_{12}$alkoxy and/or phenoxy; or $R_{16}$ is benzoyl, $C_1$–$C_{10}$haloalkylsulfonyl, camphorylsulfonyl, phenyl-$C_1$–$C_3$alkylsulfonyl, $C_3$–$C_{30}$cycloalkylsulfonyl, naphthylsulfonyl, anthracylsulfonyl or phenanthrylsulfonyl;

$R_{17}$, $R_{18}$, $R_{19}$ and $R_{20}$ independently of one another are $C_1$–$C_6$alkyl which is unsubstituted or substituted by halogen; or $R_{17}$, $R_{18}$, $R_{19}$ and $R_{20}$ are phenyl which is unsubstituted or substituted by $C_1$–$C_4$alkyl or halogen; or $R_{19}$ and $R_{20}$ together are 1,2-phenylene or $C_2$–$C_6$alkylene which is unsubstituted or substituted by $C_1$–$C_4$alkyl or halogen;

A is S, O, $NR_{13}$, or a group of formula A1, A2 or A3

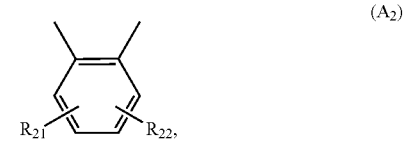

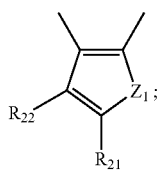
(A₃)

$R_{21}$ and $R_{22}$ independently of one other have one of the meanings given for $R_7$,
or $R_{21}$ and $R_{22}$ together are —CO—NR$_{13}$CO—,
or $R_{21}$ and $R_{22}$ together are —C(R$_{23}$)=C(R$_{24}$)—C(R$_{25}$)=C(R$_{26}$)—;
$R_{23}$, $R_{24}$, $R_{25}$ and $R_{26}$ independently of one another are hydrogen, $C_1$–$C_4$alkyl, halogen, phenyl, OR$_{13}$, SR$_{16}$, NR$_{14}$R$_{15}$, —S-phenyl, $C_2$–$C_6$alkoxycarbonyl, phenoxycarbonyl, CN, NO$_2$, $C_1$–$C_4$haloalkyl, S(O)$_n$$C_1$–$C_6$alkyl, S(O)n—$C_6$–$C_{12}$aryl, $C_1$–$C_{12}$alkyl-substituted S(O)n—$C_6$–$C_{12}$ aryl, SO$_2$O—$C_1$–$C_6$alkyl, SO$_2$O—$C_6$–$C_{10}$aryl or NHCONH$_2$;
Z is CR$_{22}$ or N; and
Z$_1$ is —CH$_2$—, S, O or NR$_{13}$.

The compounds of the formulae I and II are characterized in that they contain a carbonyl group at the o-position of the phenyl ring with respect to the benzylidene moiety.

$C_1$–$C_{18}$alkyl is linear or branched and is, for example, $C_1$–$C_{16}$—, $C_1$–$C_{12}$—, $C_1$–$C_8$—, $C_1$–$C_6$— or $C_1$–$C_4$-alkyl. Examples are methyl, ethyl, propyl, isopropyl, n-butyl, sec-butyl, isobutyl, tert-butyl, pentyl, hexyl, heptyl, 2,4,4-trimethylpentyl, 2-ethylhexyl, octyl, nonyl, decyl, undecyl, dodecyl, tetradecyl, pentadecyl, hexadecyl, heptadecyl and octadecyl, preferably $C_1$–$C_4$alkyl, such as methyl, isopropyl or butyl.

$C_1$–$C_{16}$alkyl, $C_1$–$C_{12}$alkyl, $C_1$–$C_8$alkyl, $C_1$–$C_6$alkyl and $C_1$–$C_4$alkyl are likewise linear or branched and are, for example, as defined above up to the appropriate number of carbon atoms. Of interest are, for example, $C_1$–$C_8$—, especially $C_1$–$C_6$—, preferably $C_1$–$C_4$-alkyl, such as methyl or butyl.

$C_2$–$C_{18}$alkyl, which is interrupted once or several times by —O—, is interrupted, for example, from one to five times, for example from one to three times or once or twice, by non-successive —O—. Accordingly, resulting structural units are for example: —O(CH$_2$)$_2$OH, —O(CH$_2$)$_2$OCH$_3$, —O(CH$_2$CH$_2$O)$_2$CH$_2$CH$_3$, —CH$_2$—O—CH$_3$, —CH$_2$CH$_2$—O—CH$_2$CH$_3$, —[CH$_2$CH$_2$O]$_y$—CH$_3$, wherein y=1–5, —(CH$_2$CH$_2$O)$_5$CH$_2$CH$_3$, —CH$_2$—CH(CH$_3$)—O—CH$_2$—CH$_2$CH$_3$ or —CH$_2$—CH(CH$_3$)—O—CH$_2$—CH$_3$.

$C_3$–$C_{30}$cycloalkyl is a mono- or polycyclic aliphatic ring, for example a mono-, bi- or tricyclic aliphatic ring, e.g. $C_3$–$C_{20}$—, $C_3$–$C_{18}$—, $C_3$–$C_{12}$—, $C_3$–$C_{10}$cycloalkyl. Examples of monocyclic rings are cyclopropyl, cyclobutyl, cyclopentyl, cyclohexyl, or cycloheptyl, especially cyclopentyl and cyclohexyl. Examples of polycyclic rings are perhydroanthracyl, perhydrophenyathryl, perhydronaphthyl, perhydrofluorenyl, perhydrochrysenyl, perhydropicenyl, adamantyl, bicyclo-[1.1.1]pentyl, bicyclo[4.2.2]decyl, bicyclo[2.2.2]octyl, bicyclo[3.3.2]decyl, bicyclo[4.3.2]undecyl, bicyclo[4.3.3]dodecyl, bicyclo[3.3.3]undecyl, bicyclo[4.3.1]decyl, bicyclo[4.2.1]nonyl, bicyclo[3.3.1]nonyl, bicyclo[3.2.1]octyl and the like. Also "spiro"-cycloalkyl compounds are covered by the definition $C_3$–$C_{30}$cycloalkyl in the present context, e.g. spiro[5.2]octyl, spiro[5.4]decyl, spiro[5.5]undecyl. More examples of polycyclic cycloalkyl groups, which are subject of the respective definition in the compounds of the present invention are listed in EP 878738, page 11 and 12, wherein to the formulae (1)–(46) a bond to achieve the "yl" has to be added. The person skilled in the art is aware of this fact.

In general, the cycloaliphatic rings may form repeating structural units.

$C_2$–$C_{12}$alkylene is linear or branched and is, for example, $C_2$–$C_8$—, $C_2$–$C_6$— or $C_2$–$C_4$-alkylene. Examples are ethylene, propylene, butylene, pentylene, hexylene, heptylene, octylene, nonylene, decylene, undecylene and dodecylene. Preferred is $C_2$–$C_8$alkylene, especially $C_2$–$C_6$alkylene, preferably $C_2$–$C_4$alkylene, such as ethylene or butylene.

$C_2$–$C_{12}$alkylenedisulfonyl accordingly is an alkylene radical as indicated above, which at both "yl"-moieties bears a sulfonyl group. Examples are —SO$_2$—(CH$_2$CH$_2$)$_z$—SO$_2$—, with z=1–6, e.g. —SO$_2$—CH$_2$CH$_2$—SO$_2$—, or —SO$_2$—CH(CH$_3$)CH$_2$—SO$_2$—.

Phenylenedisulfonyl, diphenylenedisulfonyl and oxydiphenylendisulfonyl also bear the sulfonyl groups at the "yl" moiety. Accordingly, resulting structures are

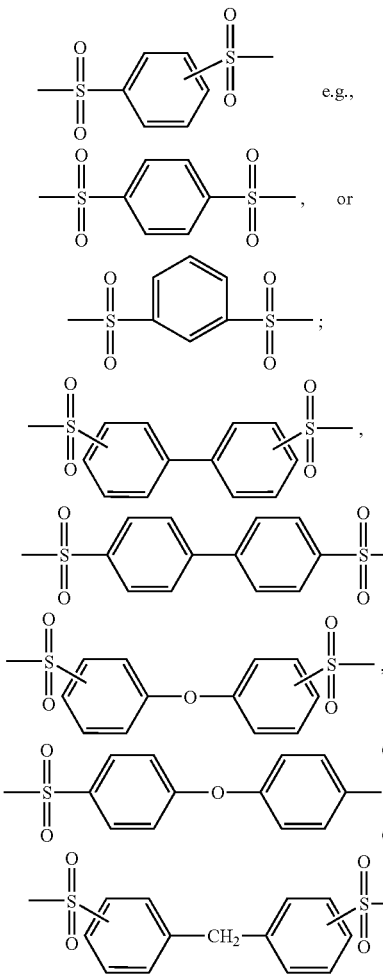

the sulfonyl groups are preferably positioned in the para-position to the methylene moiety.

Substituted phenyl carries from one to five, for example one, two or three, especially one or two, substituents on the phenyl ring. The substitution is preferably in the 4-, 3,4-, 3,5- or 3,4,5-position of the phenyl ring.

The radicals $C_1$–$C_{18}$alkyl in the group $C_1$–$C_{18}$alkylsulfonyl are meant to be linear or branched and have the meanings described above.

The radicals $C_3$–$C_{30}$cycloalkyl in the group $C_3$–$C_{30}$cyloalkylsulfonyl have the meanings described above.

When the radicals naphthyl, phenanthryl and anthracyl are substituted by one or more radicals, they are, for example, mono- to penta-substituted, for example mono-, di- or tri-substituted, especially mono- or di-substituted.

Camphoryl, 10-camphoryl, are camphor-10-yl, namely

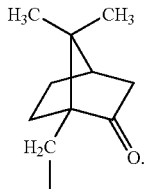

$C_2$–$C_{18}$alkanoyl is e.g. $C_2$–$C_{10}$, $C_2$–$C_8$—, $C_2$–$C_6$— or $C_2$–$C_4$alkanoyl, wherein the alkyl moiety is linear or branched. Examples ar acetyl, propionyl, butanoyl or hexanoyl, especially acetyl.

$C_1$–$C_{12}$alkoxy is e.g. $C_1$–$C_{10}$—, $C_1$–$C_8$—, $C_1$–$C_6$—, $C_1$–$C_4$alkoxy, and is linear or branched. Examples are methoxy, ethoxy, propoxy, n-butoxy, t-butoxy, octyloxy and dodecyloxy.

In $C_1$–$C_4$alkylthio the alkyl moiety is for example linear or branched. Examples are methylthio, ethylthio, propylthio or butylhtio.

$C_2$–$C_{12}$alkoxycarbonyl is ($C_1$–$C_{11}$alkyl)-O—C(O)—, wherein $C_1$–$C_{11}$alkyl is linear or branched and is as defined above up to the appropriate number of carbon atoms. Examples are $C_2$–$C_{10}$—, $C_2$–$C_8$—, $C_2$–$C_6$— or $C_2$–$C_4$alkoxycarbonyl, such as methoxycarbonyl, ethoxycarbonyl, propoxycarbonyl, butoxycarbonyl or pentoxycarbonyl.

$C_1$–$C_{10}$haloalkyl and $C_1$–$C_4$haloalkyl are for example $C_1$–$C_{10}$—, $C_1$–$C_8$—, $C_1$–$C_6$— or $C_1$–$C_4$-alkyl mono- or poly-substituted by halogen, the alkyl moieties being, for example, as defined above. There are, for example, from one to three or one or two halogen substituents at the alkyl radical. Examples are chloromethyl, trichloromethyl, trifluoromethyl or 2-bromopropyl, especially trifluoromethyl or trichloromethyl. Preferred is $C_1$–$C_{10}$fluoroalkyl.

$C_2$–$C_6$haloalkanoyl is ($C_1$–$C_5$haloalkyl)-C(O)—, wherein $C_1$–$C_5$haloalkyl is as defined above up to the appropriate number of carbon atoms. Examples are chloroacetyl, trichloroacetyl, trifluoroacetyl, pentafluoropropionyl, perfluorooctanoyl, or 2-bromopropionyl, especially trifluoroacetyl or trichloroacetyl.

Halobenzoyl is benzoyl which is mono- or poly-substituted by halogen and/or $C_1$–$C_4$haloalkyl, $C_1$–$C_4$-haloalkyl being as defined above. Examples are pentafluorobenzoyl, trichlorobenzoyl, trifluoromethylbenzoyl, especially pentafluorobenzoyl.

Halogen is fluorine, chlorine, bromine or iodine, especially chlorine or fluorine, preferably fluorine.

Phenyl-$C_1$–$C_3$alkyl is, for example, benzyl, 2-phenylethyl, 3-phenylpropyl, α-methylbenzyl or α,α-dimethylbenzyl, especially benzyl.

Oxydiphenylene is

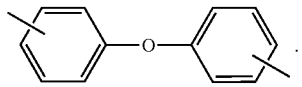

If $R_{10}$ and $R_{11}$ or $R_{14}$ and $R_{15}$ together with the nitrogen atom to which they are bonded form a 5-, 6- or 7-membered ring that optionally is interrupted by —O— or by —$NR_{13}$—, for example the following structures are obtained

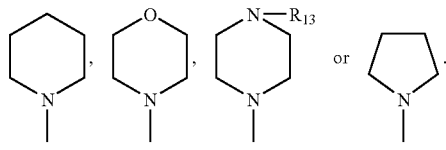

The definitions $C_1$–$C_{18}$alkylsulfonyl, phenyl-$C_1$–$C_3$alkylsulfonyl, camphorylsulfonyl, $C_1$–$C_{10}$haloalkylsulfonyl refer to the corresponding radicals $C_1$–$C_{18}$alkyl, phenyl-$C_1$–$C_3$alkyl, camphoryl and $C_1$–$C_{10}$haloalkyl, as described in detail above, being linked to a sulfonyl group (—$SO_2$—). Accordingly, also phenylsulfonyl, naphthylsulfonyl, anthracylsulfonyl and phenanthrylsulfonyl refer to the corresponding radicals linked to a sulfonyl group. $R_6$ is for example $C_2$–$C_{18}$—, $C_4$–$C_{12}$—, $C_6$–$C_{18}$—, $C_4$–$C_{10}$-alkylsulfonyl.

$C_6$–$C_{12}$aryl is for example phenyl, biphenylyl or naphthyl and $C_6$–$C_{10}$aryl is phenyl or naphthyl.

The terms "and/or" or "or/and" in the claims and throughout the specification are meant to express that not only one of the defined alternatives (substituents) may be present, but also several of the defined alternatives (substituents) together, namely mixtures of different alternatives (substituents).

The term "at least" is meant to define one or more than one, for example one or two or three, preferably one or two.

Oxime derivatives (of formulae I and II) can generally be prepared by methods described in the literature, for example by reacting suitable free oximes of formula III with the desired (for example, sulfonic) acid halides or acid anhydrides of formula IV, V or VI (for example, $R_6$Cl, $R_6$—O—$R_6$ or $C_1$—$R'_6$—Cl).

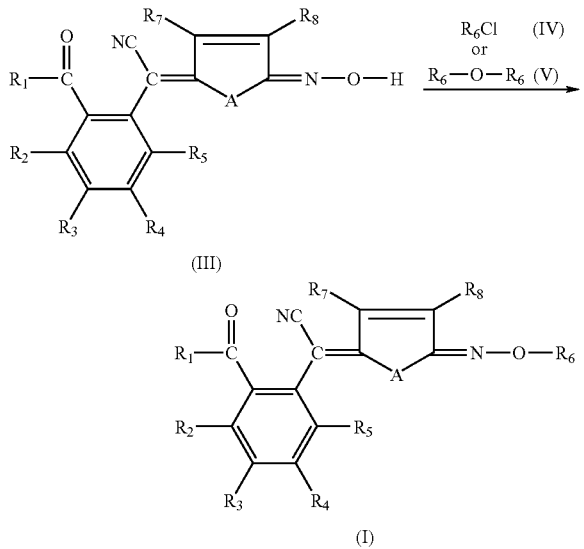

-continued

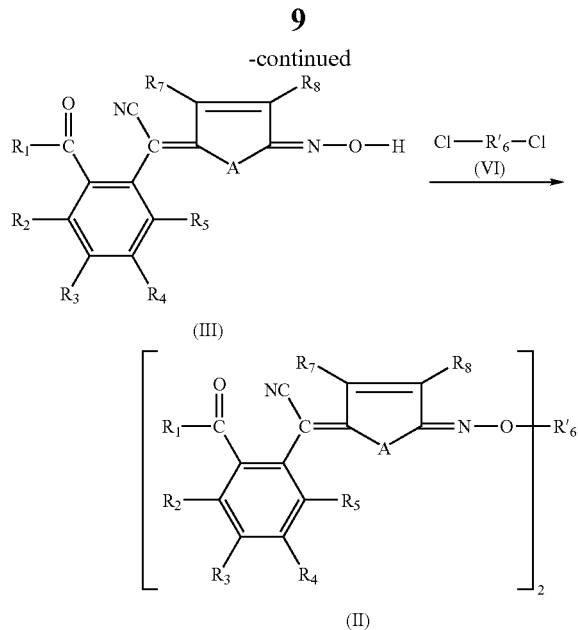

$R_1$, $R_2$, $R_3$, $R_4$, $R_5$, $R_6$ $R_7$, $R_8$ and A are defined as described above.

These reactions usually are carried out in an inert solvent such as for example toluene, methylene chloride, tetrahydrofuran (THF) or dimethylformamide (DMF) in the presence of a base, for example pyridine, a tertiary amine, such as triethylamine, or by reaction of the salt of an oxime with the desired acid chloride. These methods are disclosed, for example, in EP 48615. The sodium salts of oximes can be obtained, for example, by reacting the oxime in question with a sodium alcoholate in dimethylformamide. Such reactions are well known to those skilled in the art, and are generally carried out at temperatures in the range of −15 to +50° C., preferably 0 to 20° C.

Oxime compounds of the formula III are useful for the preparation for the oxime derivatives of the formula I and II.

Therefore, the invention also pertains to novel compounds of the formula III

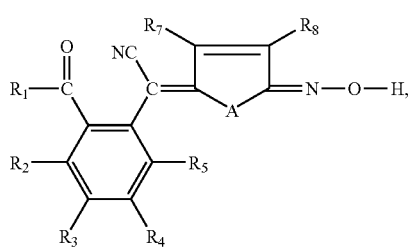

wherein
$R_1$, $R_2$, $R_3$, $R_4$, $R_5$, $R_7$, $R_8$ and A are as defined above.

The oximes of formula III required for the reaction can be prepared according to known procedures, for example by reacting benzyl cyanides or cyanomethyl heterocycles with nitrobenzenes or nitronaphtalenes in the presence of a base (such as, for example, sodium methoxide or potassium hydroxide) in a polar solvent such as, for example, methanol or DMF, as described by R. B. Davis, L. C. Pizzini & E. J. Bara, J. Org. Chem. 26, 4270 (1961) or P. Fournary and T. Marey, Bull. Soc. Chim. Fr. 3223 (1968). Temperatures of −80° C. to 80° C., especially −10° C. to 60° C. are suitable for the reaction. Phase transfer catalysis is also suitable to prepare oxime intermediates of formula III. K. Takahashi, et al. have described the use, of benzyltriethyl ammonium chloride and 50% aqueous sodium hydroxide for the reaction of nitrobenzene with benzyl cyanide (K. Takahashi, T. Tsuboi, K. Yamada, H. Iida, Nippon Kagaku Kaishi 144–7 (1976); Chemical Abstract No. 84:105162).

Oximes have also been prepared as intermediates in the synthesis of various pharmaceutical compounds (e.g. U.S. Pat. Nos. 5,043,327, 5,521,187; EP 371564, EP 541153, ES 524551) or for use as UV absorbers (for instance, in U.S. Pat. No. 3,374,248).

Oximes can also be obtained by reacting a suitable carbonyl or thionylcarbonyl compound with hydroxylamine or a hydroxylammonium salt.

The described syntheses can result in the formation of isomeric forms of the compounds of formula I and II. The double bond of the oximino group can exist in both the syn (cis, Z) and the anti (trans, E) form or as mixtures of the two geometrical isomers. In the present invention, both the individual geometrical isomers and any mixtures of two geometrical isomers can be used. The invention accordingly also relates to mixtures of isomeric forms of the compounds of formula I and II. If wanted the isomeric compounds can be seperated by the usual methods known to the person skilled in the art.

Interesting are compounds of the formula I and II, wherein A is S, or a group of formula A1 as defined above.

Interesting are further compounds of formula I and II, wherein
$R_1$ is $OR_9$ or $NR_{10}R_{11}$;
$R_2$, $R_3$, $R_4$ and $R_5$ are independently of each other hydrogen, $C_1$–$C_{12}$alkyl, halogen, $OR_{13}$ or —(CO)$OR_9$;
$R_6$ is $C_1$–$C_{10}$alkylsulfonyl, $C_1$–$C_{10}$haloalkylsulfonyl, camphorylsulfonyl, phenyl-$C_1$–$C_3$alkylsulfonyl, phenylsulfonyl, or naphthylsulfonyl, wherein the groups phenyl and naphthyl, of the radicals phenyl-$C_1$–$C_3$-alkylsulfonyl, phenylsulfonyl and naphthylsulfonyl, are unsubstituted or substituted by one or more halogen, $C_1$–$C_{16}$alkyl and/or $OR_{13}$;
$R'_8$ is phenylenedisulfonyl;
$R_7$ and $R_8$ are independently of one another hydrogen, halogen, $C_1$–$C_6$alkyl, $C_1$–$C_6$alkoxy or $OR_{13}$;
$R_9$ is hydrogen, $C_1$–$C_{18}$alkyl; or phenyl which is unsubstituted or substituted by $C_1$–$C_{18}$alkyl, halogen and/or $C_1$–$C_{12}$alkoxy;
$R_{10}$ and $R_{11}$ independently of one another are hydrogen or $C_1$–$C_{18}$alkyl; or $R_{10}$ and $R_{11}$, together with the nitrogen atom to which they are attached, form a 5-, 6- or 7-membered ring which optionally is interrupted by —O— or by —$NR_{13}$—,
$R_{13}$ is hydrogen, $C_1$–$C_{18}$alkyl or phenyl;
A is S or a group of formula A1
$R_{21}$ and $R_{22}$ independently of each other have one of the meanings given for $R_7$; and
Z is $CR_{22}$.

Especially preferred are

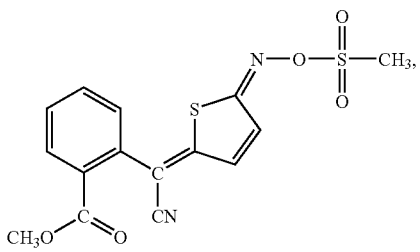

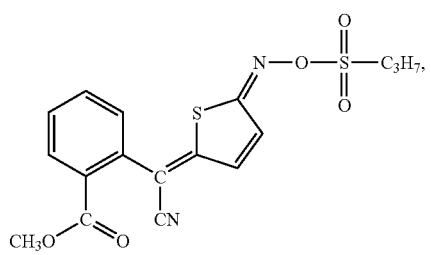
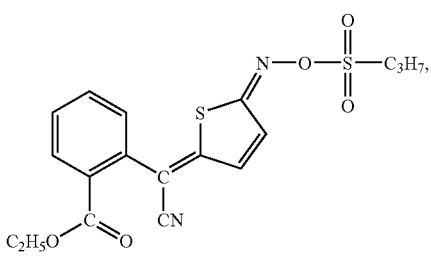
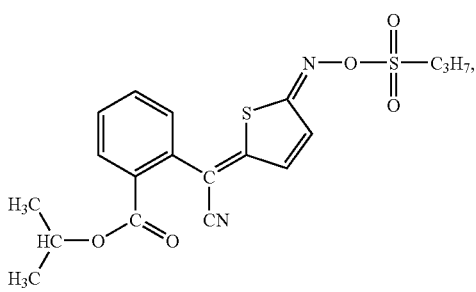
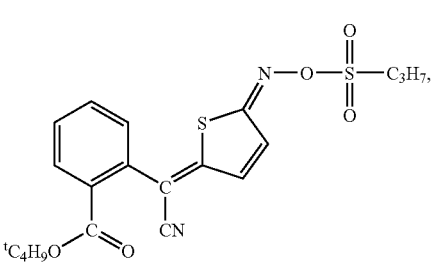
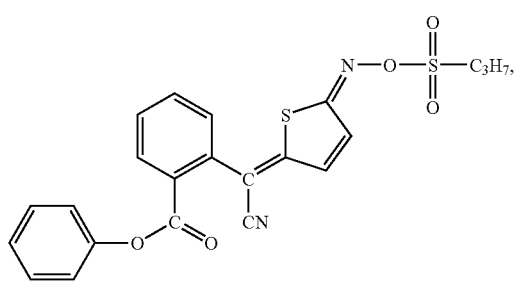
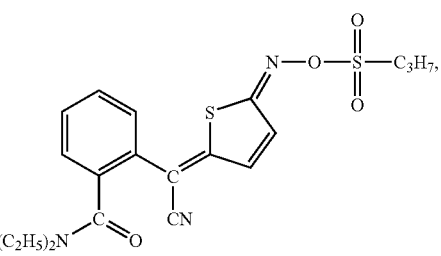
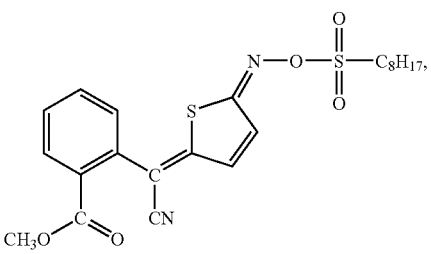
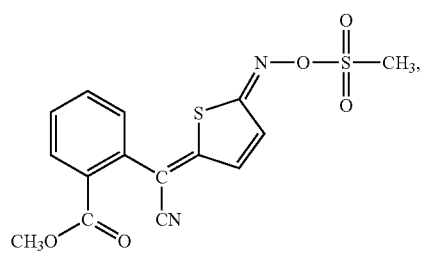
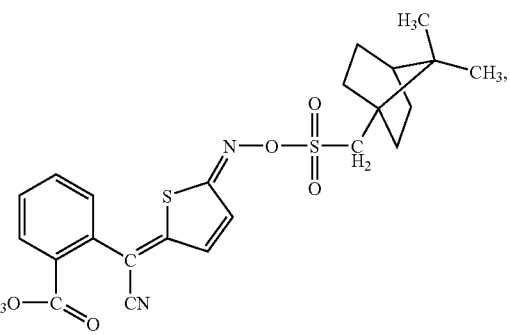
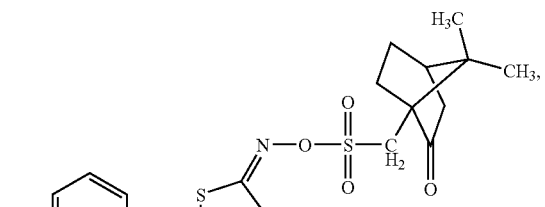
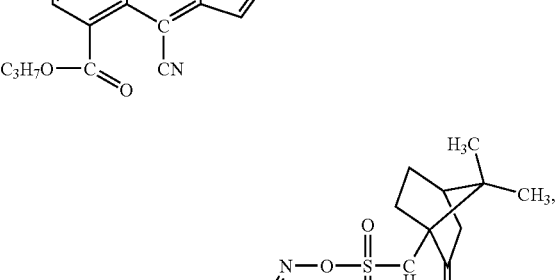
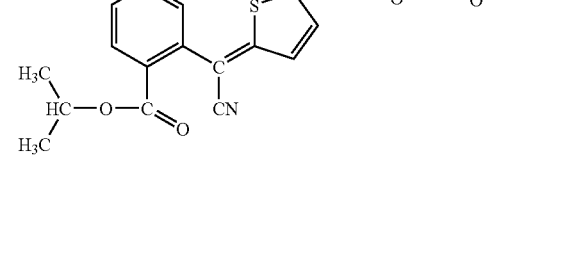

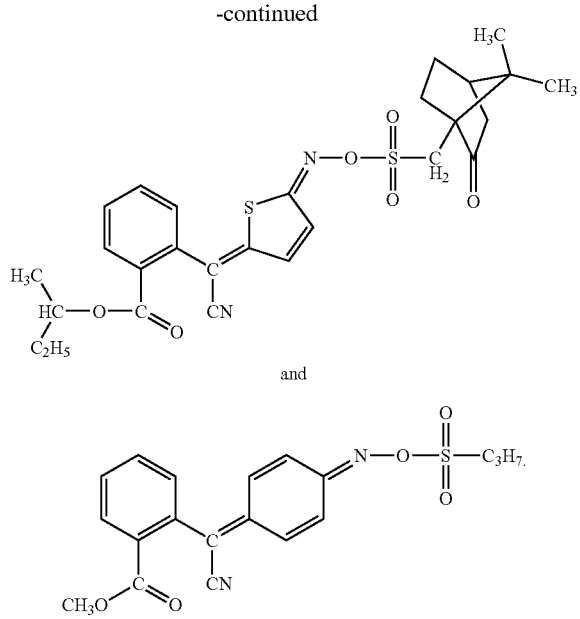

and

The compounds of the formulae I or II can be used as photosensitive acid donors in a photoresist. Resist systems can be prepared by image-wise irradiation of systems comprising compounds of formulae I or II, followed by a developing step.

The invention pertains to chemically amplified photoresist compositions comprising
(a) a compound which cures upon the action of an acid or a compound whose solubility is increased upon the action of an acid; and
(b) as photosensitive acid donor, at least one compound of the formula I or II as defined above.

A chemically amplified photoresist is understood to be a resist composition wherein the radiation sensitive component provides a catalytic amount of acid which subsequently catalyses a chemical reaction of at least one acid-sensitive component of the resist. Resulting is the induction of a solubility difference between the irradiated and non-irradiated areas of the resist. Because of the catalytic nature of this process one acid molecule can trigger reactions at multiple sites as it diffuses through the reactive polymer matrix, from one reaction site to the next, as long as it is not trapped or destroyed by any secondary reaction. Therefore, a small acid concentration is sufficient to induce a high difference in the solubility between exposed and unexposed areas in the resist. Thus, only a small concentration of the latent acid compound is necessary. As a result, resists with high contrast and high transparency at the exposure wavelength in optical imaging can be formulated, which in turn produce steep, vertical image profiles at high photosensitivity. However, as a result of this catalytic process, it is required that the latent acid catalysts are chemically and thermally very stable (as long as not irradiated) in order not to generate acid during resist storage or during processing, which—in most cases—requires a post exposure bake step to start or to complete the catalytic reaction which leads to the solubility differential. It is also required to have good solubility of the latent catalysts in the liquid resist formulation and the solid resist film to avoid any particle generation which would interfere with the application of these resists in microelectronic manufacturing processes.

In contrast, positive resist materials which are not based on the chemical amplification mechanism must contain a high concentration of the latent acid, because it is only the acid concentration which is generated from the latent acid under exposure which contributes to the increased solubility of the exposed areas in alkaline developer. Because small acid concentration has only a little effect on the change of the dissolution rate of such resist and the reaction proceeds typically without a post exposure bake here, the requirements regarding chemical and thermal stability of the latent acid are less demanding than for chemically amplified positive resists. These resists require also a much higher exposure dose to generate enough acid for achieving sufficient solubility in the alkaline developer in the exposed areas and also suffer from the relatively low optical transparency (due to the high concentration of latent acid necessary) and thus also lower resolution and sloped images. Resist compositions based on non-chemically amplified technology are therefore inferior in photosensitivity, resolution and image quality compared to chemically amplified resists.

From the above it becomes clear that chemical and thermal stability of a latent catalyst is vital for a chemically amplified resist and that latent acids which can work in a non-chemically amplified resist are not necessarily applicable to chemically amplified resists because of the different acid diffusion requirements, acid strength requirements and thermal and chemical stability requirements.

The difference in resist solubility between irradiated and non-irradiated sections that occurs as a result of the acid-catalysed reaction of the resist material during or after irradiation of the resist may be of two types depending upon which further constituents are present in the resist. If the compositions according to the invention comprise components that increase the solubility of the composition in the developer after irradiation, the resist is positive.

The invention accordingly relates to a chemically amplified positive photoresist.

If, on the other hand, the components of the formulation reduce the solubility of the composition after irradiation, the resist is negative.

The invention accordingly relates also to a chemically amplified negative photoresist.

A monomeric or polymeric compound which—in the unexposed areas—reduces the dissolution rate of an additionally present alkaline soluble binder resin in the resist formulation and which is essentially alkali-insoluble in the unexposed areas so that the resist film remains in the unexposed area after development in alkaline solution, but which is cleaved in the presence of acid, or is capable of being rearranged, in such a manner that its reaction product becomes soluble in the alkaline developer is referred to hereinafter as dissolution inhibitor.

The invention includes, as a special embodiment a chemically amplified positive alkaline-developable photoresist composition, comprising
(a1) at least one polymer having acid-labile groups which decompose in the presence of an acid and increase the solubility of the resist film in an aqueous alkaline developer solution in the exposed area and
(b) at least one compound of formula I or II.

A further embodiment of the invention is a chemically amplified positive alkaline-developable photoresist composition, comprising
(a2) at least one monomeric or oligomeric dissolution inhibitor having at least one acid-labile group which decomposes in the presence of acid and increases the solubility in an aqueous alkaline developer solution and at least one alkali-soluble polymer and,
(b) at least one compound of formula I or II.

Another specific embodiment of the invention resides in a chemically amplified positive alkaline-developable photoresist composition, comprising
(a1) at least one polymer having acid labile groups which decompose in the presence of an acid and increase the solubility in an alkaline developer in the exposed area;
(a2) a monomeric or oligomeric dissolution inhibitor, having at least one acid labile group, which decomposes in the presence of an acid and increase the alkaline solubility in the exposed area;
(a3) an alkali-soluble monomeric, oligomeric or polymeric compound at a concentration which still keeps the resist film in the unexposed area essentially insoluble in the alkaline developer, and
(b) at least one compound of formula I or II.

The invention therefore pertains to a chemically amplified photoresist composition, comprising
(a1) at least one polymer having an acid-labile group which decomposes in the presence of an acid to increase the solubility in aqueous alkaline developer solution and/or
(a2) at least one monomeric or oligomeric dissolution inhibitor having an acid-labile group which decomposes in the presence of an acid to increase the solubility in aqueous alkaline developer solution and/or
(a3) at least one alkali-soluble monomeric, oligomeric or polymeric compound; and
(b) as photosensitive acid donor, at least one compound of formula I or II.

The compositions may comprise additionally to the component (b) other photosensitive acid donors and/or (c) other additives.

Such chemically amplified positive resist systems are described, for example, in E. Reichmanis, F. M. Houlihan, O. Nalamasu, T. X. Neenan, Chem. Mater. 1991, 3, 394; or in C. G. Willson, "Introduction to Microlithography, 2nd. Ed.; L. S. Thompson, C. G. Willson, M. J. Bowden, Eds., Amer. Chem. Soc., Washington D.C., 1994, p. 139.

Suitable examples of acid-labile groups which decompose in the presence of an acid to produce aromatic hydroxy groups, carboxylic groups, keto groups and aldehyde groups and increase the solubility in aqueous alkaline developer solution are, for example, alkoxyalkyl ether groups, tetrahydrofuranyl ether groups, tetrahydropyranyl ether groups, tert.-alkyl ester groups, trityl ether groups, silyl ether groups, alkyl carbonate groups as for example tert.-butyloxycarbonyloxy-, trityl ester groups, silyl ester groups, alkoxymethyl ester groups, cumyl ester groups, acetal groups, ketal groups, tetrahydropyranyl ester groups, tetrafuranyl ester groups, tertiary alkyl ether groups, tertiary alkyl ester groups, and the like.

The polymer having functional groups capable of decomposing by the action of an acid to enhance solubility of the resist film comprising this polymer in an alkaline developing solution, which can be incorporated in the positive resist according to the present invention, may have the acid-labile groups in the backbone and/or side chains thereof, preferably in side chains thereof.

The polymer having acid-labile groups suitable for the use in the present invention can be obtained with a polymer analogous reaction where the alkaline soluble groups are partially or completely converted into the respective acid labile groups or directly by (co)-polymerization of monomers which have the acid labile groups already attached, as is for instance disclosed in EP 254853, EP 878738, EP 877293, JP-A-2-25850, JP-A-3-223860, and JP-A-4-251269.

The polymers which have acid labile groups pendant to the polymer backbone, in the present invention preferably are polymers which have, for example silylether, acetal, ketal and alkoxyalkylester groups (called "low-activation energy blocking groups") which cleave completely at relatively low post exposure bake temperatures (typically between room temperature and 110° C.) and polymers which have, for example, tert-butylester groups or tert.-butyloxycarbonyl (TBOC) groups or other ester groups which contain a secondary or tertiary carbon atom next to the oxygen atom of the ester bond (called "high-activation energy blocking groups") which need higher bake temperatures (typically >110° C.) in order to complete the deblocking reaction in the presence of acid. Hybrid systems can also be applied, wherein, both, high activation energy blocking groups as well as low activation energy blocking groups are present within one polymer. Alternatively, polymer blends of polymers, each utilizing a different blocking group chemistry, can be used in the photosensitive positive resist compositions according to the invention.

Preferred polymers which have acid labile groups are polymers and co-polymers comprising the following distinct monomer types:
1) monomers that contain acid-labile groups which decompose in the presence of an acid to increase the solubility in aqueous alkaline developer solution and
2) monomers that are free of acid labile groups and free of groups that contribute to the alkaline solubility and/or
3) monomers that contribute to aqueous alkaline solubility of the polymer.

Examples of monomers of type 1) are: non-cyclic or cyclic secondary and tertiary-alkyl (meth)acrylates such as butyl acrylate, including t-butyl acrylate, butyl methacrylate, including t-butyl methacrylate, 3-oxocyclohexyl (meth)acrylate, tetrahydropyranyl (meth)acrylate, 2-methyladamantyl (meth)acrylate, cyclohexyl (meth)acrylate, norbornyl (meth)acrylate, (2-tetrahydropyranyl) oxynorbonylalcohol acrylates, (2-tetrahydropyranyl) oxymethyltricyclododecanemethanol methacrylates, trimethylsilylmethyl (meth)acrylate, (2-tetrahydropyranyl) oxynorbonylalcohol acrylates, (2-tetrahydropyranyl) oxymethyltricyclododecanemethanol methacrylates, trimethylsilylmethyl (meth)acrylate o-/m-/p-(3-oxocyclohexyloxy)styrene, o-/m-/p-(1-methyl-1-phenylethoxy)styrene, o-/m-/p-tetrahydropyranyloxystyrene, o-/m-/p-adamantyloxystyrene, o/m-/p-cyclohexyloxystyrene, o-/m-/p-norbornyloxystyrene, non-cyclic or cyclic alkoxycarbonylstyrenes such as o-/m-/p-butoxycarbonyistyrene, including p-t-butoxycarbonylstyrene, o-/m-/p-(3-oxocyclohexyloxycarbonyl)-styrene, o-/m-/p-(1-methyl-1-phenylethoxycarbonyl)styrene, o-/m-/p-tetrahydropyranyloxycarbonylstyrene, o-/m-/p-adamantyloxycarbonylstyrene, o-/m-/p-cyclohexyloxycarbonylstyrene, o-/m-/p-norbornyloxycarbonylstyrene, non-cyclic or cyclic alkoxycarbonyloxystyrenes such as o-/m-/p-butoxycarbonyloxystyrene, including p-t-butoxycarbonyloxystyrene, o-/m-/p-(3-oxocyclohexyloxycarbonyloxy)styrene, o-/m-/p-(1-methyl-1-phenylethoxycarbonyloxy)-styrene, o-/m-/p-tetrahydropyranyloxycarbonyloxystyrene, o-/m-/p-adamantyloxycarbonyloxystyrene, o-/m-/p-cyclohexyloxycarbonyloxystyrene, o-/m-/p-norbornyloxycarbonyloxystyrene, non-cyclic or cyclic alkoxycarbonylalkoxystyrenes such aso/m/p-butoxycarbonylmethoxystyrene, p-t-butoxycarbonylmethoxystyrene, o-/m-/p-(3- oxocyclohexyloxycarbonylmethoxy)-styrene, o-/m-/p-(1-methyl-1-phenylethoxycarbonylmethoxy)styrene, o-/m-/p-tetrahydropyranyloxycarbonylmethoxystyrene, o-/m-/p-adamantyloxycarbonylmethoxystyrene, o-/m-/p-cyclohexyloxycarbonylmethoxystyrene, o-/m-/p-norbornyloxycarbonylmethoxystyrene, trimethylsiloxystyrene, dimethyl(butyl)siloxystyrene, unsaturated alkyl acetates such as isopropenyl acetate and the derivatives of thereof.

Monomers of type 1) bearing low activation energy acid labile groups include, for example, p- or m-(1-methoxy-1-methylethoxy)-styrene, p- or m-(1-methoxy-1-methylethoxy)-methylstyrene, p-or m-(1-methoxy-1-methylpropoxy)styrene, p-or m-(1-methoxy-1-methylpropoxy)methylstyrene, p- or m-(1-methoxyethoxy)-styrene, p- or m-(1-methoxyethoxy)-methylstyrene, p- or m-(1-ethoxy-1-methylethoxy)styrene, p- or m-(1-ethoxy-1-methylethoxy)-methylstyrene, p- or m-(1-ethoxy-1-methylpropoxy)styrene, p- or m-(1-ethoxy-1-methylpropoxy)-methylstyrene, p or m-(1-ethoxyethoxy) styrene, p- or m-(1-ethoxyethoxy)-methylstyrene, p-(1-ethoxyphenyl-ethoxy)styrene, p- or m-(1-n-propoxy-1-metylethoxy)styrene, p- or m-(1-n-propoxy-1-metylethoxy)-methylstyrene, p- or m-(1-n-propoxyethoxy) styrene, p- or m-(1-n-propoxyethoxy)-methylstyrene, p- or m-(1-isopropoxy-1-methylethoxy)styrene, p- or m-(1-isopropoxy-1-methylethoxy)-methylstyrene, p- or m-(1-isopropoxyethoxy)styrene, p- or m-(1-isopropoxyethoxy)-methylstyrene, p- or m-(1-isopropoxy-1-methylpropoxy) styrene, p- or m-(1-isopropoxy-1-methylporpoxy)-methylstyrene, p- or m-(1-isopropoxypropoxy)styrene, p- or m-(1-isopropoxyporpoxy)-methylstyrene, p- or m-(1-n-butoxy-1-methylethoxy)styrene, p- or m-(1-n-butoxyethoxy)styrene, p- or m-(1-isobutoxy-1-methylethoxy)styrene, p- or m-(1-tert-butoxy-1-methylethoxy)styrene, p- or m-(1-n-pentoxy-1-methylethoxy)styrene, p- or m-(1-isoamyloxy-1-methylethoxy)styrene, p- or m-(1-n-hexyloxy-1-methylethoxy)styrene, p- or m-(1-cyclohexyloxy-1-methylethoxy)styrene, p- or m-(1-trimethylsilyloxy-1-methylethoxy)styrene, p- or m-(1-trimethylsilyloxy-1-methylethoxy)-methylstyrene, p- or m-(1-benzyloxy-1-methylethoxy)styrene, p- or m-(1-benzyloxy-1-methylethoxy)-methylstyrene, p- or m-(1-methoxy-1-methylethoxy)styrene, p- or m-(1-methoxy-1-methylethoxy)-methylstyrene, p- or m-(1-trimethylsilyloxy-1-methylethoxy)styrene p- or m-(1-trimethylsilyloxy-1-methylethoxy)-methylstyrene. Other examples of polymers having alkoxyalkylester acid labile groups are given in U.S. Pat. No. 5,225,316 and EP 829766. Examples of polymers with acetal blocking groups are given in U.S. Pat. No. 5,670,299, EP 780732, U.S. Pat. Nos. 5,627,006, 5,558,976, 5,558,971, 5,468,589, EP 704762, EP 762206, EP 342498, EP 553737 and described in ACS Symp. Ser. 614, Microelectronics Technology, pp. 35–55 (1995) and J. Photopolymer Sci. Technol. Vol. 10, No. 4 (1997), pp. 571–578. The polymer used in the present invention is not limited thereto.

With respect to polymers having acetal groups as acid-labile groups, it is possible to incorporate acid labile crosslinks as for example described in H.-T. Schacht, P. Falcigno, N. Muenzel, R. Schulz, and A. Medina, ACS Symp. Ser. 706 (Micro- and Nanopatterning Polymers), p. 78–94, 1997; H.-T. Schacht, N. Muenzel, P. Falcigno, H. Holzwarth, and J. Schneider, J. Photopolymer Science and Technology, Vol.9, (1996), 573–586. This crosslinked system is preferred from the standpoint of heat resistance of the resist patterns.

Monomers with high activation energy acid labile groups are, for example, p-tert.-butoxycarbonyloxystyrene, tert.-butyl-acrylate, tert.-butyl-methacrylate, 2-methyl-2-adamantyl-methacrylate, isobornyl-methacrylate.

Examples of comonomers according to type 2) are: aromatic vinyl monomers, such as styrene, α-methylstyrene, acetoxystyrene, α-methylnaphthylene, acenaphthylene, vinyl alicyclic compounds such as vinyl norbornane, vinyl adamantane, vinyl cyclohexane, alkyl (meth)acrylates such as methyl methacrylate, acrylonitrile, vinylcyclohexane, vinylcyclohexanol, as well as maleic anhydride.

Examples of comonomers according to type 3) are: vinyl aromatic compounds such as hydroxystyrene, acrylic acid compounds such as methacrylic acid, ethylcarbonyloxystyrene and derivatives of thereof. These polymers are described, for example, in U.S. Pat. Nos. 5,827,634, 5,625,020, 5,492,793, 5,372,912, EP 660187, U.S. Pat. No. 5,679,495, EP 813113 and EP 831369. Further examples are crotonic acid, isocrotonic acid, 3-butenoic acid, acrylic acid, 4-pentenoic acid, propiolic acid, 2-butynoic acid, maleic acid, fumaric acid, and acetylenecarboxylic acid. The polymer used in the present invention is not limited thereto.

The content of acid labile monomers in the polymer may vary over a wide range and depends on the amount of the other comonomers and the alkaline solubility of the deprotected polymer. Typically, the content of monomers with acid labile groups in the polymer is between 5 and 60 mol %. If the content is too small, too low development rates and residues of the resist in the exposed areas result. If the content of acid labile monomers is too high, resist patterns are poorly defined (eroded) after development and narrow features cannot be resolved anymore and/or the resist looses its adhesion to the substrate during development. Preferably the copolymers which have acid labile groups have a $M_w$ of from about 3'000 to about 200'000, more preferably from about 5'000 to about 50'000 with a molecular weight distribution of about 3 or less, more preferably a molecular weight distribution of about 2 or less. Non-phenolic polymers, e.g. a copolymer of an alkyl acrylate such as t-butyl acrylate or t-butyl-methacrylate and a vinyl alicyclic compound, such as a vinyl norbonanyl or vinyl cyclohexanol compound, also may be prepared by such free radical polymerization or other known procedures and suitably will have a $M_w$ of from about 8'000 to about 50'000, and a molecular weight distribution of about 3 or less.

Other comonomers may suitably be added in an appropriate amount for the purpose of controlling the glass transition point of the polymer and the like.

In the present invention a mixture of two or more polymers having acid-labile groups may be used. For example, use may be made of a mixture of a polymer having acid-labile groups, which are cleaved very easily, such as acetal groups or tetrahydropyranyloxy-groups and a polymer having acid-cleavable groups, that are less easily cleaved, such as for example tertiary alkyl ester groups. Also, acid cleavable groups of different size can be combined by blending two or more polymers having different acid cleavable groups, such as a tert-butylester group and 2-methyladamantyl group or an 1-ethoxy-ethoxy group and a tetrahydropyranyloxy group. A mixture of a non-crosslinked resin and a crosslinked resin may also be used. The amount of these polymers in the present invention is preferably from 30 to 99% by weight, more preferably from 50 to 98% by weight, based on the total amount of all solid components. An alkali-soluble resin or monomeric or oligomeric compound having no acid-labile groups may be further incorporated into the composition in order to control the alkali solubility.

Examples of polymer blends with polymers having different acid-labile groups are given in EP 780732, EP 679951 and U.S. Pat. No. 5,817,444.

Preferably monomeric and oligomeric dissolution inhibitors (a2) are used in the present invention.

The monomeric or oligomeric dissolution inhibitor having the acid-labile group for use in the present invention is a compound which has at least one acid-labile group in the molecular structure, which decomposes in the presence of acid to increase the solubility in aqueous alkaline developer solution. Examples are alkoxymethyl ether groups, tetrahydrofuranyl ether groups, tetrahydropyranyl ether groups, alkoxyethyl ether groups, trityl ether groups, silyl ether groups, alkyl carbonate groups, trityl ester groups, silyl ester groups, alkoxymethyl ester groups, vinyl carbamate groups, tertiary alkyl carbamate groups, trityl amino groups, cumyl ester groups, acetal groups, ketal groups, tetrahydropyranyl ester groups, tetrafuranyl ester groups, tertiary alkyl ether groups, tertiary alkyl ester groups, and the like. The molecular weight of the acid-decomposable dissolution inhibitive compound for use in the present invention is 3'000 or lower, preferably from 100 to 3'000, more preferably from 200'to 2'500.

Examples of monomeric and oligomeric dissolution inhibitors having acid-labile groups are described as formulae (I) to (XVI) in EP 0831369. Other suitable dissolution inhibitors having acid-labile groups are shown in U.S. Pat. Nos. 5,356,752, 5,037,721, 5,015,554, JP-A-1-289946, JP-A-1-289947, JP-A-2-2560, JP-A-3-128959, JP-A-3-158855, JP-A-3-179353, JP-A-3-191351, JP-A-3-200'251, JP-A-3-200'252, JP-A-3-200'253, JP-A-3-20254, JP-A-3-200'255, JP-A-3-259149, JA-3-279958, JP-A-3-279959, JP-A-4-1650, JP-A-4-1651, JP-A-11260, JP-A-4-12356, JP-A-4-123567, JP-A-1-289946, JP-A-3-128959, JP-A-3-158855, JP-A-3-179353, JP-A-3-191351, JP-A-3-200'251, JP-A-3-200'252, JP-A-3-200'253, JP-A-3-200'254, JP-A-3-200'255, JP-A-3-259149, JA-3-279958, JP-A-3-279959, JP-A-4-1650, JP-A-4-1651, JP-A-11260, JP-A-4-12356, JP-A-4-12357 and Japanese Patent Applications Nos. 3-33229, 3-230790,3-320438, 4-254157, 4-52732, 4-103215, 4-104542, 4-107885, 4-107889, 4-152195, 4-254157, 4-103215, 4-104542, 4-107885, 4-107889, and 4-152195.

The composition can also contain polymeric dissolution inhibitors, for example, polyacetals as described for example in U.S. Pat. No. 5,354,643 or poly-N,O-acetals for example those described in U.S. Pat. No. 5,498,506, either in combination with an alkaline soluble polymer, or in combination with a polymer containing acid labile groups which increase the solubility of the resist film in the developer after exposure, or with a combination of both types of polymers.

In the case where the dissolution inhibitor having acid-labile groups is used in the present invention in combination with the oxime derivatives of formula I or II, the alkali-soluble polymer and/or the polymer having acid-labile groups, the amount of the dissolution inhibitor is from 3 to 55% by weight, preferably from 5 to 45% by weight, most preferably from 10 to 35% by weight, based on the total amount of all solid components of the photosensitive composition.

A polymer soluble in an aqueous alkali solution (a3) is preferably used in the present invention. Examples of these polymers include novolak resins, hydrogenated novolak resins, acetone-pyrogallol resins, poly(o-hydroxystyrene), poly(m-hydroxystyrene), poly(p-hydroxystyrene), hydrogenated poly(hydroxystyrene)s, halogen-or alkyl-substituted poly(hydroxystyrene)s, hydroxystyrene/N-substituted maleimide copolymers, o/p- and m/p-hydroxystyrene copolymers, partially o-alkylated poly(hydroxystyrene)s, [e.g., o-methylated, o-(1-methoxy)ethylated, o-(1-ethoxy) ethylated, o-2-tetrahydropyranylated, and o-(t-butoxycarbonyl)methylated poly(hydroxystyrene)s having a degree of substitution of from 5 to 30 mol % of the hydroxyl groups], o-acylated poly(hydroxystyrene)s [e.g., o-acetylated and o-(t-butoxy)carbonylated poly (hydroxystyrene)s having a degree of substitution of from 5 to 30 mol % of the hydroxyl groups], styrene/maleic anhydride copolymers, styrene/hydroxystyrene copolymers, c-methylstyrene/hydroxystyrene copolymers, carboxylated methacrylic resins, and derivatives thereof. Further suitable are poly (meth)acrylic acid [e.g. poly(acrylic acid)], (meth) acrylic acid/(meth)acrylate copolymers [e.g. acrylic acid/methyl acrylate copolymers, methacrylic acid/methyl methacrylate copolymers or methacrylic acid/methyl methacrylate/t-butyl methacrylate copolymers], (meth) acrylic acid/alkene copolymers [e.g. acrylic acid/ethylene copolymers], (meth)acrylic acid/(meth)acrylamide copolymers (e.g. acrylic acid/acrylamide copolymers, (meth) acrylic acid/vinyl chloride copolymers [e.g. acrylic acid/ vinyl chloride copolymers], (meth)acrylic acid/vinyl acetate copolymer [e.g. acrylic acid/vinyl acetate copolymers], maleic acid/vinyl ether copolymers [e.g. maleic acid/methyl vinyl ether copolymers], maleic acid mono ester/methyl vinyl ester copolymers [e.g. maleic acid mono methyl ester/ methyl vinyl ether copolymers], maleic acid/(meth)acrylic acid copolymers [e.g. maleic acid/acrylic acid copolymers or maleic acid/methacrylic acid copolymers), maleic acid/ (meth)acrylate copolymers (e.g. maleic acid/methyl acrylate copolymers], maleic acid/vinyl chloride copolymers, maleic acid/vinyl acetate copolymers and maleic acid/alkene copolymers [e.g. maleic acid/ethylene copolymers and maleic acid/1-chloropropene copolymers]. However, the alkali-soluble polymer for use in the present invention should not be construed as being limited to these examples.

Especially preferred alkali-soluble polymers (a3) are novolak resins, poly(o-hydroxystyrene), poly(m-hydroxystyrene), poly(p-hydroxystyrene), copolymers of the respective hydroxystyrene monomers, for example with p-vinylcyclohexanol, alkyl-substituted poly (hydroxystyrene)s, partially o- or m-alkylated and o- or m-acylated poly(hydroxystyrene)s, styrene/hydroxystyrene copolymer, and α-methylstyrene/hydroxystyrene copolymers. The novolak resins are obtained by addition-condensing one or more given monomers as the main ingredient with one or more aldehydes in the presence of an acid catalyst.

Examples of monomers useful in preparing alkaline soluble resins include hydroxylated aromatic compounds such as phenol, cresols, i.e., m-cresol, p-cresol, and o-cresol, xylenols, e.g., 2,5-xylenol, 3,5-xylenol, 3,4-xylenol, and 2,3-xylenol, alkoxyphenols, e.g., p-methoxyphenol, m-methoxyphenol, 3,5-dimethoxyphenol, 2-methoxy-4-methylphenol, m-ethoxyphenol, p-ethoxyphenol, m-propoxyphenol, p-propoxyphenol, m-butoxyphenol, and p-butoxyphenol, dialkylphenols, e.g., 2-methyl-4-isopropylphenol, and other hydroxylated aromatics including m-chlorophenol, p-chlorophenol, o-chlorophenol, dihydroxybiphenyl, bisphenol A, phenylphenol, resorcinol, and naphthol. These compounds may be used alone or as a mixture of two or more thereof. The main monomers for novolak resins should not be construed as being limited to the above examples.

Examples of the aldehydes for polycondensation with phenolic compounds to obtain novolaks include formaldehyde, p-formaldehyde, acetaldehyde, propionaldehyde, benzaldehyde, phenylacetaldehyde, α-phenylpropionaldehyde, β-phenylpropionaldehyde, o-hydroxybenzaldehyde, m-hydroxybenzaldehyde, p-hydroxybenzaldehyde, o-chlorobenzaldehyde, m-chlorobenzaldehyde, p-chlorobenzaldehyde, o-nitrobenzaldehyde, m-nitrobenzaldehyde, o-methylbenzaldehyde, m-methylbenzaldehyde, p-methylbenzaldehyde, p-ethylbenzaldehyde, p-n-butylbenzaldehyde, furfural, chloroacetaldehyde, and acetals derived from these, such as chloroacetaldehyde diethyl acetal. Preferred of these is formaldehyde.

These aldehydes may be used alone or in combination of two or more thereof. Examples of the acid catalyst include hydrochloric acid, sulfuric acid, formic acid, acetic acid, and oxalic acid.

The weight-average molecular weight of the thus-obtained novolak resin suitably is from 1'000 to 30'000. If the weight-average molecular weight thereof is lower than 1'000, the film reduction at unexposed parts during development is liable to be large. If the weight-average molecular weight there of exceeds 50'000, the developing rate may be too low. The especially preferred range of the molecular weight of the novolak resin is from 2'000 to 20'000.

The poly(hydroxystyrene)s and derivatives and copolymers thereof shown above as alkali-soluble polymers other than novolak resins each have a weight-average molecular weight of 2'000 or higher, preferably from 4'000 to 200'000, more preferably from 5'000 to 50'000. From the standpoint of obtaining a polymer film having improved heat resistance, the weight-average molecular weight thereof is desirably at least 5'000 or higher.

Weight-average molecular weight in the context of the present invention is meant to be the one determined by gel permeation chromatography and calibrated for with polystyrene standard.

In the present invention the alkali-soluble polymers may be used as a mixture of two or more thereof. In the case where a mixture of an alkali-soluble polymer and the polymer having groups which decompose by the action of an acid to enhance solubility in an alkaline developing solution is used, the addition amount of the alkali-soluble polymer is preferably up to 80% by weight, more preferably up to 60% by weight, most preferably up to 40% by weight, based on the total amount of the photosensitive composition (excluding the solvent). The amount exceeding 80% by weight is undesirable because the resist pattern suffers a considerable decrease in thickness, resulting in poor images and low resolution.

In the case where an alkali-soluble polymer is used together with a dissolution inhibitor, without the polymer having groups which decompose by the action of an acid, to enhance solubility in an alkaline developing solution, the amount of the alkali-soluble polymer is preferably from 40% to 90% by weight, more preferably from 50 to 85% by weight, most preferably 60 to 80% by weight. If the amount thereof is smaller than 40% by weight, undesirable results such as reduced sensitivity are caused. On the other hand, if it exceeds 90% by weight, the resist pattern suffers a considerable decrease in film thickness, resulting in poor resolution and image reproduction.

The content of the oxime derivatives of formula I or II, (component (b)) in the positive resist according to the present invention is preferably between 0.01% to 20% by weight, based on the total amount of all solid components in the photoresist.

The use of the oxime derivatives according to the invention in chemically amplified systems, which operates on the principle of the removal of a protecting group from a polymer, generally produces a positive resist. Positive resists are preferred over negative resists in many applications, especially because of their higher resolution. There is, however, also interest in producing a negative image using the positive resist mechanism, in order to combine the advantages of the high degree of resolution of the positive resist with the properties of the negative resist. This can be achieved by introducing a so-called image-reversal step as described, for example, in EP 361906. For this purpose, the image-wise irradiated resist material is before the developing step treated with, for example, a gaseous base, thereby image-wise neutralizing the acid which has been produced. Then, a second irradiation, over the whole area, and thermal aftertreatment are carried out and the negative image is then developed in the customary manner.

Acid-sensitive components that produce a negative resist characteristically are especially compounds which, when catalysed by an acid (e.g. the acid formed during irradiation of the compounds of formulae I or II), are capable of undergoing a crosslinking reaction with themselves and/or with one or more further components of the composition. Compounds of this type are, for example, the known acid-curable resins, such as, for example, acrylic, polyester, alkyd, melamine, urea, epoxy and phenolic resins or mixtures thereof. Amino resins, phenolic resins and epoxy resins are very suitable. Acid-curable resins of this type are generally known and are described, for example, in "Ullmann's Encyclopädie der technischen Chemie" [Ullmanns Enceclopedia of Technical Chemistry], 4th Edition, Vol. 15 (1978), p. 613–628. The crosslinker components should generally be present in a concentration of from 2 to 40, preferably from 5 to 30, percent by weight, based on the total solids content of the negative resist composition.

The invention thus includes, as a special embodiment, chemically amplified negative, alkali-developable photoresists, comprising (a4) an alkali-soluble resin as binder (a5) a component that when catalysed by an acid undergoes a crosslinking reaction with itself and/or with the binder, and (b) as photosensitive acid donor an oxime derivative of formula I or II.

The composition may comprise additionally to the component (b) other photosensitive acid donors and/or (c) other additives.

Especially preferred as acid-curable resins (a5) are amino resins, such as non-etherified or etherified melamine, urea, guanidine or biuret resins, especially methylated melamine resins or butylated melamine resins, corresponding glycolurils and urones. By "resins" in this context, there are to be understood both customary technical mixtures, which generally also comprise oligomers, and pure and high purity compounds. N-hexa(methoxymethyl)melamine and tetramethoxymethyl glucoril and N,N'-dimethoxymethylurone are the acid-curable resins given the greatest preference.

The concentration of the compound of formula I or II in negative resists in general is from 0.1 to 30, preferably up to 20, percent by weight, based on the total solids content of the compositions. From 1 to 15 percent by weight is especially preferred.

Where appropriate, the negative compositions may comprise a film-forming polymeric binder (a4). This binder is preferably an alkali-soluble phenolic resin. Well suited for this purpose are, for example, novolaks, derived from an aldehyde, for example acetaldehyde or furfuraldehyde, but especially from formaldehyde, and a phenol, for example unsubstituted phenol, mono- or di-chlorosubstituted phenol, such as p-chlorophenol, phenol mono- or di-substituted by $C_1$–$C_9$alkyl, such as o-, m- or p-cresol, the various xylenols, p-tert-butylphenol, p-nonylphenol, p-phenylphenol, resorcinol, bis(4-hydroxyphenyl)methane or 2,2-bis(4-hydroxyphenyl)propane. Also suitable are homo- and co-polymers based on ethylenically unsaturated phenols, for example homopolymers of vinyl- and 1-propenyl-substituted phenols, such as p-vinylphenol or p-(1-propenyl) phenol or copolymers of these phenols with one or more ethylenically unsaturated materials, for example styrenes. The amount of binder should generally be from 30 to 95 percent by weight or, preferably, from 40 to 80 percent by weight.

An especially preferred negative resist composition comprises from 0.5 to 15 percent by weight of an oxime derivative of formula I or II (component (b)), from 40 to 99 percent by weight of a phenolic resin as binder (component (a4)), for example one of those mentioned above, and from 0.5 to 30 percent by weight of a melamine resin (component (a5)) as crosslinking agent, the percentages relating to the solids content of the composition. With novolak or especially with polyvinyl phenol as binder, a negative resist having especially good properties is obtained.

Oxime derivatives can also be used as acid generators, which can be activated photochemically, for the acid-catalysed crosslinking of, for example, poly(glycidyl) methacrylates in negative resist systems. Such crosslinking reactions are described, for example, by Chae et al. in Pollimo 1993, 17(3), 292.

The positive and the negative resist compositions may comprise in addition to the photosensitive acid donor compound of formula I or II further photosensitive acid donor compounds (b1), further additives (c), other photoinitiators (d), and/or sensitizers (e).

Therefore, subject of the invention also are chemically amplified resist compositions as described above, in addition to components (a) and (b), or components (a1), (a2), (a3) and (b), or components (a4), (a5) and (b) comprising further additives (c), further photosensitive acid donor compounds (b1), other photoinitiators (d), and/or sensitizers (e).

Oxime derivatives of the present invention in the positive and negative resist can also be used together with other, known photolatent acids (b1), for example, onium salts, 6-nitrobenzylsulfonates, bis-sulfonyl diazomethane compounds, cyano group-containing oximesulfonate compounds., etc. Examples of known photolatent acids for chemically amplified resists are described in U.S. Pat. Nos. 5,731,364, 5,800,964, EP 704762, U.S. Pat. Nos. 5,468,589, 5,558,971, 5,558,976, 6,004,724, GB 2348644 and particularly in EP 794457 and EP 795786.

If a mixture of photolatent acids is used in the resist compositions according to the invention, the weight ratio of oxime derivatives of formula I or II to the other photolatent acid (b1) in the mixture is preferably from 1:99 to 99:1.

Examples of photolatent acids which are suitable to be used in admixture with the compounds of formula I and II are (1) onium salt compounds, for example, iodonium salts, sulfonium salts, phosphonium salts, diazonium salts, pyridinium salts. Preferred are diphenyliodonium triflate, diphenyliodonium pyrenesulfonate, diphenyliodonium dodecylbenzenesulfonate, triphenylsulfonium triflate, triphenylsulfonium hexafluoroantimonate, diphenyliodonium hexafluoroantimonate, triphenylsulfonium naphthalenesulfonate, (hydroxyphenyl) benzylmethylsulfonium toluenesulfonate and the like.

Particularly preferred are triphenylsulfonium triflate, diphenyliodonium hexafluoroantimonate.

(2) halogen-containing compounds haloalkyl group-containing heterocyclic compounds, haloalkyl group-containing hydrocarbon compounds and the like. Preferred are (trichloromethyl)-s-triazine derivatives such as phenyl-bis(trichloromethyl)-s-triazine, methozyphenyl-bis(trichloromethyl)-s-triazine, naphthyl-bis (trichloromethyl)-s-triazine and the like; 1.1-bis(4-chlorophnyl)-2,2,2-trichloroethane; and the like.

(3) sulfone compounds, for example β-ketosulfones, β-sulfonylsulfones and their α-diazo derivatives and the like. Preferred are phenacylphenylsulfone, mesitylphenacylsulfone, bis(phenylsulfonyl)methane, bis (phenylsulfonyl)diazomethane.

(4) sulfonate compounds, for example alkylsulfonic acid esters, haloalkylsulfonic acid esters, arylsulfonic acid esters, iminosulfonates, imidosulfonates and the like. Preferred imidosulfonate compounds are, for example, N-(trifluoromethlsulfonyloxy)succinimide, N-(trifluoromethylsulfonyloxy)phthalimide, N-(trifluoromethylsulfonyloxy)naphthylimide, N-(trifluoromethylsulfonyloxy)diphenylmaleimide, N-(trifluoromethylsulfonyloxy)-bicyclo-[2,2,1]-hept-5-ene-2,3-dicarboximide, N-(trifluoromethylsulfonyloxy)-7-oxabicyclo-[2,2,1]-hept-5-ene-2,3-dicarboximide, N-(trifluoromethylsulfonyloxy)-7-oxabicyclo-[2,2,1]-hept-5-ene-2,3-dicarboximide, N-(trifluoromethylsulfonyloxy)-bicyclo-[2,2,1]-heptan-5, 6-oxy-2,3-dicarboximide, N-(camphanylsulfonyloxy) succinimide, N-(camphanylsulfonyloxy)phthalimide, N-(camphanylsulfonyloxy)naphthylimide, N-(camphanylsulfonyloxy)diphenylmaleimide, N-(camphanylsulfonyloxy)bicyclo-[2,2,1]-hept-5-ene-2, 3-dicarboximide, N-(camphanylsulfonyloxy)-7-oxabicyclo-[2,2,1]-hept-5-ene-2,3-dicarboximide, N-(camphanylsulfonyloxy)-7-oxabicyclo-[2,2,1]hept-5-ene-2,3-dicarboximide, N-(camphanylsulfonyloxy)-bicyclo-[2,2,1]-heptan-5,6-oxy-2,3-dicarboximide, N-(4-methylphenylsulfonyloxy)succinimide, N-(4-methylphenylsulfonyloxy)phthalimide, N-(4-methylphenylsulfonyloxy)naphthylimide, N-(4-methylphenylsulfonyloxy)naphthylimide, N-(4-methylphenylsulfonyloxy)diphenylmaleimide, N-(4-methylphenylsulfonyloxy)-bicyclo-[2,2,1]-hept-5-ene-2, 3-dicarboximide, N-(4-methylphenylsulfonyloxy)-7-oxabicyclo-[2,2,1]-hept-5-ene-2,3-dicarboximide, N-(4-methylphenylsulfonyloxy)-bicyclo-[2,2,1]-heptan-5,6-oxy-2,3-dicarboximide, N-(2-trifluoromethylphenylsulfonyloxy)succinimide, N-(2-trifluoromethylphenylsulfonyloxy)naphthylimide, N-(2-trifluoromethylphenylsulfonyloxy)diphenylmaleimide, N-(2-trifluoromethylphenylsulfonyloxy)-bicyclo-[2,2,1]-hept-5-ene-2,3-dicarboximide, N-(2-trifluoromethylphenylsulfonyloxy)-7-oxabicyclo-[2,2,1]-hept-5-ene-2,3-dicarboximide, N-(2-trifluoromethylphenylsulfonyloxy)-bicyclo-[2,2,1]-heptan-5,6-oxy-2,3-dicarboximide and the like.

Other suitable sulfonate compounds preferably are, for example, benzoin tosylate, pyrogallol tristriflate, pyrogallolomethanesulfonic acid triester, nitrobenzyl-9,10-diethyoxyanthracene-2-sulfonate, α-(4-toluene-sulfonyloxyimino)-benzyl cyanide, α-(4-toluene-sulfonyloxyimino)-4-methoxybenzyl cyanide, α-(4-toluene-sulfonyloxyimino)-2-thienylmethyl cyanide, α-(methanesulfonyloxyimino)-1-cyclohexenylacetonitrile, α-(butylsulfonyloxyimino)-1-cyclopentenylacetonitrile, (4-methylsulfonyloxyimino-cyclohexa-2,5-dienylidene)-phenyl-acetonitrile, (5-methylsulfonyloxyimino-5H-thiophen-2-ylidene)-phenyl-acetonitrile, (5-methylsulfonyloxyimino-5H-thiophen-2-ylidene)-(2-methylphenyl)-acetonitrile, (5-propylsulfonyloxyimino-5H-thiophen-2-ylidene)-(2-methylphenyl)-acetonitrile, (5-methylsulfonyloxyimino-5H-thiophen-2-ylidene)-(2-chlorophenyl)-acetonitrile and the like.

In the radiation sensitive resin composition of this invention, particularly preferred sulfonate compounds include pyrogallolmethanesulfonic acid triester, N-(trifluoromethylsulfonyloxy)bicyclo-[2,2,1]-hept-5-ene-2,3-dicarboximide, N-(camphanylsulfonyloxy)naphthylimide, N-(2-trifluoromethylphenylsulfonyloxy)phthalimide, N-(trifluoromethylsulfonyloxy)-bicyclo-[2,2,1]-hept-5-ene-2,3-dicarboximide, N-(camphanylsulfonyloxy)naphthylimide, N-(2-trifluoromethylphenylsulfonyloxy)phthalimide and the like.

(5) Quinonediazide compounds, for example 1,2-quinonediazidesulfonic acid ester compounds of polyhydroxy compounds. Preferred are compounds having a 1,2-quinonediazidesulfonyl group, e.g. a 1,2-benzoquinonediazide-4-sulfonyl group, a 1,2-naphthoquinonediazide-4-sulfonyl group, a 1,2-naphthoquinonediazide-5-sulfonyl group, a 1,2-naphthoquinonediazide-6-sulfonyl group or the like. Particularly preferred are compounds having a 1,2-naphthoquinonediazide-4-sulfonyl group or a 1,2-naphthoquinonediazide-5-sulfonyl group. In particular suitable are 1,2-quinonediazidesulfonic acid esters of (poly) hydroxyphenyl aryl ketones such as 2,3,4-trihydroxybenzophenone, 2,4,6-trihydroxybenzophenone, 2,3,4,4'-tetrahydroxybenzophenone, 2,2',3,4-tetrahydroxybenzophenone, 2,3,4,4'-tetrahydroxybenzophenone, 2,2',4,4'-tetrahydroxybenzophenone 2,2',3,4,-4'-pentahydroxybenzophenone, 2,2'3,2,6'-pentahydroxybenzophenone, 2,3,3',4,4'5'-hexahydroxybenzophenone, 2,3',4,4',5'6'-hexahydroxybenzophenone and the like; 1,2-quinonediazidesulfonic acid esters of bis-[(poly) hydroxyphenyl]alkanes such as bis(4-hydroxyphenyl)ethane, bis(2,4-dihydroxyphenyl)ethane, 2,2-bis(4-hydroxyphenyl)propane, 2,2-bis(2,4-dihydroxyphenyl)propane, 2,2-bis-(2,3,4-tridroxyphenyl)propane and the like; 1,2-quinonediazidesulfonic acid esters of (poly) hydroxyphenylalkanes such as 4,4'-dihydroxytriphenylmethane, 4,4'4"-trihydroxytriphenylmethane, 4,4'5,5'-tetramethyl-2,2'2"-trihydroxytriphenylmethane, 2,2,5,5'-tetramethyl-4,4',4"-trihydroxytriphenylmethane, 1,1,1-tris(4-hydroxyphenyl)ethane, 1,1-bis(4-hydroxyphenyl)-1-phenylethane, 1,1-bis(4-hydroxyphenyl)-1-(4-[1-(hydroxyphenyl)-1-methylethyl]phenyl)ethane and the like; 1,2-quinonediazidesulfonic acid esters of (poly) hydroxyphenylflavans such as 2,4,4-trimethyl-2',4',7-trihydroxy-2-phenylflavan, 2,4,4-trimethyl-2',4',5',6,7-pentahydroxy-2-phenylflavan and the like.

The positive and negative photoresist composition of the present invention may optionally contain one or more additives (c) customarily used in photoresists in the customary amounts known to a person skilled in the art, for example, dyes, pigments, plasticizers, surfactants, flow improvers, wetting agents, adhesion promoters, thixotropic agents, colourants, fillers, solubility accelerators, acid-amplifier, photosensitizers and organic basic compounds. Further examples for organic basic compounds which can be used in the resist composition of the present invention are compounds which are stronger bases than phenol, in particular, nitrogen-containing basic compounds. These compounds may be ionic, like, for example, tetraalkylammonium salts or non-ionic. Preferred organic basic compounds are nitrogen-containing basic compounds having, per molecule, two or more nitrogen atoms having different chemical environments. Especially preferred are compounds containing both at least one substituted or unsubstituted amino group and at least one nitrogen-containing ring structure, and compounds having at least one alkylamino group. Examples of such preferred compounds include guanidine, aminopyridine, amino alkylpyridines, aminopyrrolidine, indazole, imidazole, pyrazole, pyrazine, pyrimidine, purine, imidazoline, pyrazoline, piperazine, aminomorpholine, and aminoalkylmorpholines. Suitable are both, the unsubstituted compounds or substituted derivatives thereof. Preferred substituents include amino, aminoalkyl groups, alkylamino groups, aminoaryl groups, arylamino groups, alkyl groups alkoxy groups, acyl groups acyloxy groups aryl groups, aryloxy groups, nitro, hydroxy, and cyano. Specific examples of especially preferred organic basic compounds include guanidine, 1,1-dimethylguanidine, 1,1,3,3-tetramethylguanidine, 2-aminopyridine, 3-aminopyridine, 4-aminopyridine, 2-dimethylaminopyridine, 4-dimethylaminopyridine, 2-diethylaminopyridine, 2-(aminomethyl)pyridine, 2-amino-3-methylpyridine, 2-amino-4-methylpyridine, 2-amino-5-methylpyridine, 2-amino-6-methylpyridine, 3-aminoehtylpyridine, 4-aminoethylpyridine, 3-aminopyrrolidine, piperazine, N-(2-aminoethyl)piperazine, N-(2-aminoethyl)piperidine, 4-amino-2,2,6,6-tetramethylpiperidine, 4-piperidinopiperidine, 2-imimopiperidine, 1-(2-aminoethyl)pyrrolidine, pyrazole, 3-amino-5-methylpyrazole, 5-amino-3-methyl-1-p-tolylpyrazole, pyrazine, 2-(aminomethyl)-5-methylpyrazine, pyrimidine, 2,4-diaminopyrimidine, 4,6-dihydroxypyrimidine, 2-pyrazoline, 3-pyrazoline, N-aminomorpholine, and N-(2-aminoethyl)morpholine.

Other examples of suitable organic basic compounds are described in DE 4408318, U.S. Pat. Nos. 5,609,989, 5,556,734, EP 762207, DE 4306069, EP 611998, EP 813113, EP 611998 and U.S. Pat. No. 5,498,506. However, the organic basic compounds suitable in the present invention are not limited to these examples.

The nitrogen-containing basic compounds may be used alone or in combination of two or more thereof. The added amount of the nitrogen-containing basic compounds is usually from 0.001 to 10 parts by weight, preferably from 0.01 to 5 parts by weight, per 100 parts by weight of the photosensitive resin composition (excluding the solvent). If the amount thereof is smaller than 0.001 part by weight, the effects of the present invention cannot be obtained. On the other hand, if it exceeds 10 parts by weight, reduced sensitivity and impaired developability at unexposed parts are liable to be caused.

The composition can further contain a basic organic compound which decomposes under actinic radiation ("suicide base") such as for example described in EP 710885, U.S. Pat. Nos. 5,663,035, 5,595,855, 5,525,453, and EP 611998.

Examples of dyes (c) suitable for the compositions of the present invention are oil-soluble dyes and basic dyes, e.g. Oil Yellow #101, Oil Yellow #103, Oil Pink #312, Oil Green BG, Oil Blue BOS, Oil Blue #603, Oil Black BY, Oil Black BS, Oil Black T-505 (all manufactured by Orient Chemical Industries Ltd., Japan), crystal violet (CI42555), methyl violet (CI 42535), rhodamine B (CI 45170B), malachite green (CI 4200+), and methylene blue (CI52015).

Spectral sensitizers (e) may be further added to sensitize the photo latent acid to exhibit absorption in a region of longer wavelengths than far ultaviolet, whereby the photosensitive composition of the present invention can, for example, be rendered sensitive to an i-line or g-line radiation. Examples of suitable spectral sensitizers include benzophenones, p,p'-tetramethyldiaminobenzophenone, p,p'-tetraethylethylaminobenzophenone, thioxanthone, 2-chlorothioxanthone, anthrone, pyrene, perylene, phenothiazine, benzil, acridine orange, benzoflavin, cetoflavin T, 9,10-diphenylanthracene, 9-fluorenone, acetophenone, phenanthrene, 2-nitrofluorene, 5-nitroacenaphthene, benzoquinone, 2-chloro-4-nitroaniline, N-acetyl-p-nitroaniline, p-nitroaniline, N-acetyl-4-nitro-1-naphthylamine, picramide, anthraquinone, 2-ethylanthraquinone, 2-tert-butylanthraquinone, 1,2-benzanthraquinone, 3-methyl-1,3-diaza-1,9-benzanthrone, dibenzalacetone, 1,2-naphthoquinone, 3-acylcoumarin derivatives, 3,3'-carbonyl-bis(5,7-dimethoxycarbonylcoumarin), 3-(aroylmethylene) thiazolines, eosin, rhodamine, erythrosine, and coronene. However, the suitable spectral sensitizers are not limited to these examples.

These spectral sensitizers can be used also as light absorbers for absorbing the far ultraviolet emitted by a light source. In this case, the light absorber reduces light reflection from the substrate and lessens the influence of multiple reflection within the resist film, thereby diminishing the effect of standing waves.

Further suitable additives (c) are "acid-amplifiers", compounds that accelerate the acid formation or enhance the acid concentration. Such compounds may also be used in combination with the oxime derivatives of the formulae I or II according to the invention in positive or negative resists, or in imaging systems as well as in all coating applications. Such acid amplifiers are described e.g. in Arimitsu, K. et al. J. Photopolym. Sci. Technol. 1995, 8, pp 43; Kudo, K. et al. J. Photopolym. Sci. Technol. 1995, 8, pp 45; Ichimura, K. et al. Chem: Letters 1995, pp 551.

Usually, for the application to a substrate of the photosensitive composition of the present invention, the composition is dissolved in an appropriate solvent. Preferred examples of these solvents include ethylene dichloride, cyclohexanone, cyclopentanone, 2-heptanone, γ-butyrolactone, methyl ethyl ketone, ethylene glycol monomethyl ether, ethylene glycol monoethyl ether, 2-methoxyethyl acetate, 2-ethoxyethyl acetate, 2-ethoxyethanol, diethyl glycol dimethyl ether, ethylene glycol monoethyl ether acetate, propylene glycol monomethyl ether, propylene glycol monomethyl ether acetate, toluene, ethyl acetate, methyl lactate, ethyl lactate, methyl methoxypropionate, ethyl ethoxypropionate, methylpyruvate, ethyl pyruvate, propyl pyruvate, N,N-dimethylformamide, dimethyl sulfoxide, N-methylpyrrolidone, and tetrahydrofuran. These solvents may be used alone or as mixtures. Preferred examples of the solvents are esters, such as 2-methoxyethyl acetate, ethylene glycolmonoethyl ether acetate, propylene glycol monomethyl ether acetate, methyl methoxypropionate, ethyl ethoxypropionate, and ethyl lactate. Use of such solvents is advantageous because the oxime derivatives represented by formulae I or II according to the present invention have good compatibility therewith and better solubility therein.

A surfactant can be added to the solvent. Examples of suitable surfactants include nonionic surfactants, such as polyoxyethylene alkyl ethers, e.g. polyoxyethylene lauryl ether, polyoxyethylene stearyl ether, polyoxyethylene acetyl ether, and polyoxyethylene oleyl ether; polyoxyethylene alkylaryl ethers, e.g. polyoxyethylene, octylphenol ether and polyoxyethylene nonylphenol ether; polyoxyethylene/polyoxypropylene block copolymers, sorbitan/fatty acid esters, e.g. sorbitan monolaurate, sorbitan monopalmitate, sorbitan monostearate, sorbitan monooleate, sorbitan trioleate; fluorochemical surfactants such as F-top EF301, EF303, and EF352 (manufactured by New Akita Chemical Company, Japan). Megafac F171 and F17.3 (manufactured by Dainippon Ink & Chemicals, Inc., Japan), Fluorad FC 430 and FC431 (manufactured by Sumitomo 3M Ltd., Japan), Asahi Guard AG710 and Surflon S-382, SC101, SC102, SC103, SC104, SC105, and SC106 (manufactured by Asahi Grass Col, Ltd., Japan); organosiloxane polymer KP341 (manufactured by Shin-Etsu Chemical Co., Ltd., Japan); and acrylic or methacrylic (co)polymers Poly-flow Now.75 and NO.95 (manufactured by Kyoeisha Chemical Co., Ltd., Japan). The added amount of the surfactant usually is 2 parts by weight or lower, desirably 0.5 part by weight or lower, per 100 parts by weight of the solid components of the composition of the present invention. The surfactants may be added alone or in combination of two or more thereof.

The solution is uniformly applied to a substrate by means of known coating methods, for example by spin-coating, immersion, knife coating, curtain pouring techniques, brush application, spraying and roller coating. It is also possible to apply the photosensitive layer to a temporary, flexible support and then to coat the final substrate by coating transfer (laminating).

The amount applied (coating thickness) and the nature of the substrate (coating substrate) are dependent on the desired field of application. The range of coating thicknesses can in principle include values from approximately 0.01 μm to more than 100 μm.

After the coating operation generally the solvent is removed by heating, resulting in a layer of the photoresist on the substrate. The drying temperature must of course be lower than the temperature at which certain components of the resist might react or decompose. In general, drying temperatures are in the range from 60 to 160° C.

The resist coating is then irradiated image-wise. The expression "image-wise irradiation" includes irradiation in a predetermined pattern using actinic radiation, i.e. both irradiation through a mask containing a predetermined pattern, for example a transparency, a chrome mask or a reticle, and irradiation using a laser beam or electron beam that writes directly onto the resist surface, for example under the control of a computer, and thus produces an image. Another way to produce a pattern is by interference of two beams or images as used for example in holographic applications. It is also possible to use masks made of liquid crystals that can be addressed pixel by pixel to generate digital images, as is, for example described by A. Bertsch; J. Y. Jezequel; J. C. Andre in Journal of Photochemistry and Photobiology A: Chemistry 1997, 107 pp. 275–281 and by K. P. Nicolay in Offset Printing 1997, 6, pp. 34–37.

After the irradiation and, if necessary, thermal treatment, the irradiated sites (in the case of positive resists) or the non-irradiated sites (in the case of negative resists) of the composition are removed in a manner known per se using a developer.

In order to accelerate the catalytic reaction and hence the development of a sufficient difference in solubility between the irradiated and unirradiated sections of the resist coating in the developer, the coating is preferably heated before being developed. The heating can also be carried out or begun during the irradiation. Temperatures of from 60 to 160° C. are preferably used. The period of time depends on the heating method and, if necessary, the optimum period can be determined easily by a person skilled in the art by means of a few routine experiments. It is generally from a few seconds to several minutes. For example, a period of from 10 to 300 seconds is very suitable when a hotplate is used and from 1 to 30 minutes when a convection oven is used. It is important for the latent acid donors according to the invention in the unirradiated sites on the resist to be stable under those processing conditions.

The coating is then developed, the portions of the coating that, after irradiation, are more soluble in the developer being removed. If necessary, slight agitation of the workpiece, gentle brushing of the coating in the developer bath or spray developing can accelerate that process step. The aqueous-alkaline developers customary in resist technology may, for example, be used for the development. Such developers comprise, for example, sodium or potassium hydroxide, the corresponding carbonates, hydrogen carbonates, silicates or metasilicates, but preferably metal-free bases, such as ammonia or amines, for example ethylamine, n-propylamine, diethylamine, di-n-propylamine, triethylamine, methyl diethylamine, alkanolamines, for example dimethyl ethanolamine, triethanolamine, quaternary ammonium hydroxides, for example tetramethylammonium hydroxide or tetraethylammonium hydroxide. The developer solutions are generally up to 0.5 N, but are usually diluted in suitable manner before use. For example solutions having a normality of approximately 0.1–0.3 are well suited. The choice of developer depends on the nature of the photocurable surface coating, especially on the nature of the binder used or of the resulting photolysis products. The aqueous developer solutions may, if necessary, also comprise relatively small amounts of wetting agents and/or organic solvents. Typical organic solvents that can be added to the developer fluids are, for example, cyclohexanone, 2-ethoxyethanol, toluene, acetone, isopropanol and also mixtures of two or more of these solvents. A typical aqueous/organic developer system is based on Butylcellosolve$^{RTM}$/water.

Subject of the invention also is a process for the preparation of a photoresist by
(1) applying to a substrate a composition as described above;
(2) post apply baking the composition at temperatures between 60° C. and 160° C.;
(3) image-wise irradiating with light of wavelengths between 150 nm and 1500 nm;
(4) optionally post exposure baking the composition at temperatures between 60° C. and 160° C.; and
(5) developing with a solvent or with an aqueous alkaline developer.

Preferred is a process, wherein the image-wise irradiation is carried out with monochromatic or polychromatic radiation in the wavelength range from 190 to 450 nm, in particular in the range from 190 to 260 nm.

The photoresist compositions can be used on all substrates and with all exposure techniques known to the person skilled in the art. For example, semiconductor substrates can be used, such as silicon, gallium arsenide, germanium, indium antimonide; furthermore substrate covered by oxide or nitride layers, such as silicon dioxide, silicon nitride, titanium nitride, siloxanes, as well as metal substrates and metal coated substrates with metals such as aluminium, copper, tungsten, etc. The substrate can also be coated with polymeric materials, for example with organic antireflective coatings, insulation layers and dielectric coatings from polymeric materials prior to coating with the photoresist.

The photoresist layer can be exposed by all common techniques, such as direct writing, i.e. with a laser beam or projection lithography in step- and repeat mode or scanning mode, or by contact printing through a mask.

In case of projection lithography a wide range of optical conditions can be used such as coherent, partial coherent or incoherent irradiation. This includes off-axis illumination techniques, for example annular illumination and quadrupol illumination where the radiation is allowed to pass only certain regions of the lens, excluding the lens center.

The mask used to replicate the pattern can be a hard mask or a flexible mask. The mask can include transparent, semitransparent and opaque patterns. The pattern size can include also patterns which are at or below the resolution limit of the projection optics and placed on the mask in a certain way in order to modify the aerial image, intensity and phase modulation of the irradiation after having passed the mask. This includes phase shift masks and half-tone phase shift masks.

The patterning process of the photoresist composition can be used to generate patterns of any desired geometry and shape, for example dense and isolated lines, contact holes, trenches, dots, etc.

The photoresists according to the invention have excellent lithographic properties, in particular a high sensitivity, and high resist transparency for the imaging radiation.

Possible areas of use of the composition according to the invention are as follows: use as photoresists for electronics, such as etching resists, ion-implantation resist, electroplating resists or solder resists, the manufacture of integrated circuits or thin film transistor-resist (TFT); the manufacture of printing plates, such as offset printing plates or screen printing stencils, use in the etching of mouldings or in stereolithography or holography techniques. The coating substrates and processing conditions vary accordingly.

The compositions according to the invention are also outstandingly suitable as coating compositions for substrates of all types, including wood, textiles, paper, ceramics, glass, plastics, such as polyesters, polyethylene terephthalate, polyolefins or cellulose acetate, especially in the form of films, but especially for coating metals, such as Ni, Fe, Zn, Mg, Co or especially Cu and Al, and also Si, silicon oxides or nitrides, to which an image is to be applied by means of image-wise irradiation.

The invention relates also to the use of compounds of formula I or II as photolatent acid donors in compositions that can be crosslinked under the action of an acid and/or as dissolution enhancers in compositions wherein the solubility is increased under the action of an acid.

Subject of the invention further is a process of crosslinking compounds that can be crosslinked under the action of an acid, which method comprises adding a compound of formula I and/or II to the above-mentioned compounds and irradiating imagewise or over the whole area with light having a wavelength of 150–1500 nm.

The invention relates also to the use of compounds of formulae I or II as photosensitive acid donors in the preparation of surface coatings, printing inks, printing plates, dental compositions, colour filters, resists or image-recording materials, or image-recording materials for recording holographic images, as well as to a process for the preparation of surface coatings, printing inks, printing plates, dental compositions, colour filters, resists, image-recording materials, or image-recording materials for recording holographic images.

Subject of the invention is also the use of compounds of formulae I or II as photosensitive acid donors in the preparation of colour filters or chemically amplified resist materials; as well as to a process for the preparation of colour filters or chemically amplified resist materials.

As already mentioned above, in photocrosslinkable compositions, oxime derivatives act as latent curing catalysts: when irradiated with light they release acid which catalyses the crosslinking reaction. In addition, the acid released by the radiation can, for example, catalyse the removal of suitable acid-sensitive protecting groups from a polymer structure, or the cleavage of polymers containing acid-sensitive groups in the polymer backbone. Other applications are, for example, colour-change systems based on a change in the pH or in the solubility of, for example, a pigment protected by acid-sensitive protecting groups.

Oxime derivatives according to the present invention can also be used to produce so-called "print-out" images when the compound is used together with a colourant that changes colour when the pH changes, as described e.g. in JP Hei 4 328552-A or in U.S. Pat. No. 5,237,059. Such color-change systems can be used according to EP 199672 also to monitor goods that are sensitive to heat or radiation.

In addition to a colour change, it is possible during the acid-catalysed deprotection of soluble pigment molecules (as described e.g. in EP 648770, EP 648817 and EP 742255) for the pigment crystals to be precipitated; this can be used in the production of colour filters as described e.g. in EP 654711 or print out images and indicator applications, when the colour of the latent pigment precursor differs from that of the precipitated pigment crystal.

Compositions using pH sensitive dyes or latent pigments in combination with oxime derivatives can be used as indicators for electromagnetic radiation, such as gamma radiation, electron beams, UV- or visible light, or simple throw away dosimeters. Especially for light, that is invisible to the human eye, like UV- or IR-light, such dosimeters are of interest.

Finally, oxime derivatives that are sparingly soluble in an aqueous-alkaline developer can be rendered soluble in the developer by means of light-induced conversion into the free acid, with the result that they can be used as solubility enhancers in combination with suitable film-forming resins.

Resins which can be crosslinked by acid catalysis and accordingly by the photolatent acids of formula I or II according to the invention, are, for example, mixtures of polyfunctional alcohols or hydroxy-group-containing acrylic and polyester resins, or partially hydrolysed polyvinylacetals or polyvinyl alcohols with polyfunctional acetal derivatives. Under certain conditions, for example the acid-catalysed self-condensation of acetal-functionalised resins is also possible.

Suitable acid-curable resins in general are all resins whose curing can be accelerated by acid catalysts, such as aminoplasts or phenolic resole resins. These resins are for example melamine, urea, epoxy, phenolic, acrylic, polyester and alkyd resins, but especially mixtures of acrylic, polyester or alkyd resins with a melamine resin. Also included are modified surface-coating resins, such as acrylic-modified polyester and alkyd resins. Examples of individual types of resins that are covered by the expression acrylic, polyester and alkyd resins are described, for example, in Wagner, Sarx, Lackkunstharze (Munich, 1971), pp. 86–123 and pp. 229–238, or in Ullmann, Encyclopädie der techn. Chemie, 4th Ed., Vol. 15 (1978), pp. 613–628, or Ullmann's Encyclopedia of Industrial Chemistry, Verlag Chemie, 1991, Vol. 18, p. 360 ff., Vol. A19, p. 371 ff.

In coating applications the surface coating preferably comprises an amino resin. Examples thereof are etherified or non-etherified melamine, urea, guanidine or biuret resins. Acid catalysis is especially important in the curing of surface coatings comprising etherified amino resins, such as methylated or butylated melamine resins (N-methoxymethyl- or N-butoxymethyl-melamine) or methylated/butylated glycolurils. Examples of other resin compositions are mixtures of polyfunctional alcohols or hydroxy-group-containing acrylic and polyester resins, or partially hydrolysed polyvinyl acetate or polyvinyl alcohol with polyfunctional dihydropropanyl derivatives, such as derivatives of 3,4-dihydro-2H-pyran-2-carboxylic acid. Polysiloxanes can also be crosslinked using acid catalysis. These siloxane group-containing resins can, for example, either undergo self-condensation by means of acid-catalysed hydrolysis or be crosslinked with a second component of the resin, such as a polyfunctional alcohol, a hydroxy-group-containing acrylic or polyester resin, a partially hydrolysed polyvinyl acetal or a polyvinyl alcohol. This type of polycondensation of polysiloxanes is described, for example, in J. J. Lebrun, H. Pode, Comprehensive Polymer Science, Vol. 5, p. 593, Pergamon Press, Oxford, 1989. Other cationically polymerisable materials that are suitable for the preparation of surface coatings are ethylenically unsaturated compounds polymerisable by a cationic mechanism, such as vinyl ethers, for example methyl vinyl ether, isobutyl vinyl ether, trimethylolpropane trivinyl ether, ethylene glycol divinyl ether; cyclic vinyl ethers, for example 3,4-dihydro-2-formyl-2H-pyran (dimeric acrolein) or the 3,4-dihydro-2H-pyran-2-carboxylic acid ester of 2-hydroxymethyl-3,4-dihydro-2H-pyran; vinyl esters, such as vinyl acetate and vinyl stearate, mono- and di-olefins, such as α-methylstyrene, N-vinylpyrrolidone or N-vinylcarbazole.

For certain purposes, resin mixtures having monomeric or oligomeric constituents containing polymerisable unsaturated groups are used. Such surface coatings can also be cured using compounds of formula I or II. In that process, radical polymerisation initiators or photoinitiators can additionally be used. The former initiate polymerisation of the unsaturated groups during heat treatment, the latter during UV irradiation.

The invention also relates to a composition comprising
(a) a compound which cures upon the action of an acid or a compound whose solubility is increased upon the action of an acid; and
(b) as photosensitive acid donor, at least one compound of the formula I or II as described above.

The compounds of formulae I or II respectively, are generally added to the compositions in an amount from 0.1 to 30% by weight, for example from 0.5 to 10% by weight, especially from 1 to 5% by weight.

According to the invention, the compounds of formula I or II can be used together with further photosensitive acid donor compounds (b1), further photoinitiators (d), sensitisers (e) and/or additives (c).

Suitable photosensitive acid donor compounds (b1), sensitizers (e) and addtives (c) are described above.

Examples of additional photoinitiators (d) are radical photoinitiators, such as those from the class of the benzophenones, acetophenone derivatives, such as a-hydroxycycloalkylphenyl ketone, dialkoxyacetophenone, a-hydroxy- or a-amino-acetophenone, 4-aroyl-1,3-dioxolans, benzoin alkyl ethers and benzil ketals, monoacylphosphine oxides, bisacylphosphine oxides or titanocenes. Examples of especially suitable additional photoinitiators are: 1-(4-dodecylbenzoyl)-1-hydroxy-1-methylethane, 1-(4-isopropylbenzoyl)-1-hydroxy-1-methyl-ethane, 1-benzoyl-1-hydroxy-1-methyl-ethane, 1-[4-(2-hydroxyethoxy)-benzoyl]-1-hydroxy-1-methyl-ethane, 1-[4-(acryloyloxyethoxy)-benzoyl]-1-hydroxy-1-methyl-ethane, diphenyl ketone, phenyl-1-hydroxy-cyclohexyl ketone, (4-morpholinobenzoyl)-1-benzyl-1-dimethylamino-propane, 1-(3,4-dimethoxyphenyl)-2-benzyl-2-dimethylamino-butan-1-one, (4-methylthiobenzoyl)-1-methyl-1-morpholino-ethane, benzil dimethyl ketal, bis(cyclopentadienyl)-bis(2,6-difluoro-3-pyrryl-phenyl) titanium, trimethylbenzoyidiphenylphosphine oxide, bis(2,6-dimethoxy-benzoyl)-(2,4,4-trimethyl-pentyl)-phosphine oxide, bis(2,4,6-trimethylbenzoyl)-2,4-dipentyloxyphenylphosphine oxide or bis(2,4,6-trimethylbenzoyl)phenyl-phosphine oxide. Further suitable additional photoinitiators are to be found in U.S. Pat. No. 4,950,581, column 20, line 35 to column 21, line 35. Other examples are trihalomethyltriazine derivatives or hexaaryl-bisimidazolyl compounds. Further examples for additional photoinitiators are borate compounds, as for example described in U.S. Pat. No. 4,772,530, EP 775706, GB 2307474, GB 2307473 and GB 2304472. The borate compounds preferably are used in combination with electron acceptor compounds, such as, for example dye cations, or thioxanthone derivatives.

Further examples of additional photoinitiators are peroxide compounds, e.g. benzoyl peroxide (other suitable peroxides are described in U.S. Pat. No. 4,950,581, col. 19, l. 17–25) or cationic photoinitiators, such as aromatic sulfonium or iodonium salts, such as those to be found in U.S. Pat. No. 4,950,581, col. 18, l. 60 to col. 19, l. 10, or cyclopentadienyl-arene-iron(II) complex salts, for example ($\eta^6$-isopropylbenzene)($\eta^5$-cyclopentadienyl)-iron(II) hexafluorophosphate.

The surface coatings may be solutions or dispersions of the surface-coating resin in an organic solvent or in water, but they may also be solventless. Of special interest are surface coatings having a low solvent content, so-called "high solids surface coatings", and powder coating compositions. The surface coatings may be clear lacquers, as used, for example, in the automobile industry as finishing lacquers for multilayer coatings. They may also comprise pigments and/or fillers, which may be inorganic or organic compounds, and metal powders for metal effect finishes.

The surface coatings may also comprise relatively small amounts of special additives customary in surface-coating technology, for example flow improvers, thixotropic agents, leveling agents, antifoaming agents, wetting agents, adhesion promoters, light stabilisers, antioxidants, or sensitisers.

UV absorbers, such as those of the hydroxyphenyl-benzotriazole, hydroxyphenyl-benzophenone, oxalic acid amide or hydroxyphenyl-s-triazine type may be added to the compositions according to the invention as light stabilisers. Individual compounds or mixtures of those compounds can be used with or without the addition of sterically hindered amines (HALS).

Examples of such UV absorbers and light stabilisers are
1. 2-(2'-Hydroxyphenyl)-benzotriazoles, such as 2-(2'-hydroxy-5'-methylphenyl)-benzotriazole, 2-(3',5'-di-tert-butyl-2'-hydroxyphenyl)-benzotriazole, 2-(5'-tert-butyl-2'-hydroxyphenyl)-benzotriazole, 2-(2'-hydroxy-5'-(1,1,3,3-tetramethylbutyl)phenyl)-benzotriazole, 2-(3',5'-di-t-butyl-2'-hydroxyphenyl)-5-chloro-benzotriazole, 2-(3'-tert-butyl-2'-hydroxy-5'-methylphenyl)-5-chloro-benzotriazole, 2-(3'-sec-butyl-5'-tert-butyl-2'-hydroxyphenyl)-benzotriazole, 2-(2'-hydroxy-4'-octyloxyphenyl)-benzotriazole, 2-(3',5'-di-tert-amyl-2'-hydroxyphenyl)-benzotriazole, 2-(3',5'-bis-(a,a-dimethylbenzyl)-2'-hydroxyphenyl)-benzotriazole, mixture of 2-(3'-tert-butyl-2'-hydroxy-5'-(2-octyloxycarbonylethyl)phenyl)-5-chloro-benzotriazole, 2-(3'-tert-butyl-5'-[2-(2-ethyl-hexyloxy)-carbonylethyl]-2'-hydroxyphenyl)-5-chloro-benzotriazole, 2-(3'-tert-butyl-2'-hydroxy-5'-(2-methoxycarbonylethyl)phenyl)-5-chloro-benzotriazole, 2(3'-tert-butyl-2'-hydroxy-5'-(2-methoxycarbonylethyl)phenyl)-benzotriazole, 2-(3'-tert-butyl-2'-hydroxy-5'-(2-octyloxycarbonylethyl)phenyl)-benzotriazole, 2-(3'-tert-butyl-5'-[2-(2-ethylhexyloxy)carbonylethyl]-2'-hydroxyphenyl)-benzotriazole, 2-(3'-dodecyl-2'-hydroxy-5'-methylphenyl)-benzotriazole and 2-(3'-tert-butyl-2'-hydroxy-5'-(2-isooctyloxycarbonylethyl)phenyl-benzotriazole, 2,2'-methylene-bis[4-(1,1,3,3-tetramethylbutyl)-6-benzotriazol-2-yl-phenol]; transesterification product of 2-[3'-tert-butyl-5'-(2-methoxycarbonylethyl)-2'-hydroxyphenyl]benzotriazole with polyethylene glycol 300; [R—CH$_2$CH$_2$—COO(CH$_2$)$_3$]$_2$— wherein R=3'-tert-butyl-4'-hydroxy-5'-2H-benzotriazol-2-yl-phenyl.
2. 2-Hydroxybenzophenones, such as the 4-hydroxy, 4-methoxy, 4-octyloxy, 4-decyloxy, 4-dodecyloxy, 4-benzyloxy, 4,2',4'-trihydroxy or 2'-hydroxy-4,4'-dimethoxy derivative.
3. Esters of unsubstituted or substituted benzoic acids, such as 4-tert-butyl-phenyl salicylate, phenyl salicylate, octylphenyl salicylate, dibenzoylresorcinol, bis(4-tert-butylbenzoyl)resorcinol, benzoylresorcinol, 3,5-di-tert-butyl-4-hydroxybenzoic acid 2,4-di-tert-butylphenyl ester, 3,5-di-tert-butyl-4-hydroxybenzoic acid hexadecyl ester, 3,5-di-tert-butyl-4-hydroxybenzoic acid octadecyl ester, 3,5-di-tert-butyl-4-hydroxybenzoic acid 2-methyl-4,6-di-tert-butylphenyl ester.
4. Acrylates, such as a-cyano-b,b-diphenylacrylic acid ethyl ester or isooctyl ester, a-carbomethoxy-cinnamic acid methyl ester, a-cyano-b-methyl-p-methoxy-cinnamic acid methyl ester or butyl ester, a-carbomethoxy-p-methoxy-cinnamic acid methyl ester, N-(b-carbomethoxy-b-cyanovinyl)-2-methyl-indoline.
5. Sterically hindered amines, such as bis(2,2,6,6-tetramethyl-piperidyl)sebacate, bis(2,2,6,6-tetramethyl-piperidyl)succinate, bis(1,2,2,6,6-pentamethylpiperidyl)sebacate, n-butyl-3,5-di-tert-butyl-4-hydroxybenzyl-malonic acid bis(1,2,2,6,6-pentamethylpiperidyl)ester, condensation product of 1-hydroxyethyl-2,2,6,6-tetramethyl-4-hydroxypiperidine and succinic acid, condensation product of N,N'-bis(2,2,6,6-tetramethyl-4-piperidyl)hexamethylenediamine and 4-tert-octylamino-2,6-dichloro-1,3,5-s-triazine, tris(2,2,6,6-tetramethyl-4-piperidyl)nitrilotriacetate, tetrakis(2,2,6,6-tetramethyl-4-piperidyl)-1,2,3,4-butanetetraoate, 1,1'-(1,2-ethanediyl)-bis(3,3,5,5-tetramethyl-piperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazaspiro[4.5]decane-2,4-dione, bis(1-octyloxy-2,2,6,6-tetramethylpiperidyl)sebacate, bis(1-octyloxy-2,2,6,6-tetramethylpiperidyl)succinate, condensation product of N,N'-bis(2,2,6,6-tetra-methyl-4-piperidyl)hexamethylenediamine and 4-morpholino-2,6-dichloro-1,3,5-triazine, condensation product of 2-chloro-4,6-di(4-n-butylamino-2,2,6,6-tetramethylpiperidyl)-1,3,5-triazine and 1,2-bis(3-aminopropylamino)ethane, condensation product of 2-chloro-4,6-di(4-n-butylamino-1,2,2,6,6-pentamethylpiperidyl)-1,3,5-triazine and 1,2-bis(3- aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl) pyrrolidine-2,5-dione, 3-dodecyl-1-(1,2,2,6,6-pentamethyl-4-piperidyl)-pyrrolidine-2,5-dione.
6. Oxalic acid diamides, such as 4,4'-dioctyloxy-oxanilide, 2,2'-diethoxy-oxanilide, 2,2'-di-octyloxy-5,5'-di-tert-butyl-oxanilide, 2,2'-didodecyloxy-5,5'-di-tert-butyl-oxanilide, 2-ethoxy-2'-ethyl-oxanilide, N,N'-bis(3-dimethylaminopropyl)oxalamide, 2-ethoxy-5-tert-butyl-2'-ethyloxanilide and a mixture thereof with 2-ethoxy-2'-ethyl-5,4'-di-tert-butyl-oxanilide, mixtures of o- and p-methoxy- and of o- and p-ethoxy-di-substituted oxanilides.
7. 2-(2-Hydroxyphenyl)-1.3.5-triazines, such as 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-trazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-[2-hydroxy-4-(2-hydroxy-3-butyloxy-propyloxy)phenyl]4,6-bis(2,4-dimethyl-phenyl)-1,3,5-triazine, 2-[2-hydroxy-4-(2-hydroxy-3-octyloxy-propyloxy)phenyl]-4,6-bis(2,4-dimethylphenyl)-1,3,5-triazine, 2-[4-dodecyl-/trdecyl-oxy-(2-hydroxypropyl) oxy-2-hydroxy-phenyl]-4,6-bis(2,4-dimethylphenyl)-1,3, 5-triazine.
8. Phosphites and phosphonites, such as triphenyl phosphite, diphenyl alkyl phosphites, phenyl dialkyl phosphites, tris(nonylphenyl)phosphite, trilauryl phosphite, trioctadecyl phosphite, distearyl-pentaerythritol diphosphite, tris (2,4-di-tert-butylphenyl)phosphite, diisodecylpentaerythritol diphosphite, bis(2,4-di-tert-butylphenyl) pentaerythritol diphosphite, bis(2,6-di-tert-butylmethylphenyl)pentaerythritol diphosphite, bis-isodecyloxy-pentaerythritol diphosphite, bis(2,4-di-tert-butyl-6-methylphenyl)pentaerythritol diphosphite, bis-(2, 4,6-tri-tert-butylphenyl)pentaerythritol diphosphite, tristearyl-sorbitol triphosphite, tetrakis(2,4-di-tert-butylphenyl)-4,4'-biphenylene diphosphonite, 6-isooctyloxy-2,4,8,10-tetra-tert-butyl-12H-dibenzo[d, g]-1,3,2-dioxaphosphocine, 6-fluoro-2,4,8,10-tetra-tert-butyl-12-methyl-dibenzo[d,g]-1,3,2-dioxaphosphocine, bis(2,4-di-tert-butyl-6-methylphenyl)methyl phosphite, bis(2,4-di-tert-butyl-6-methylphenyl)ethyl phosphite.

Such light stabilisers can also be added, for example, to an adjacent surface-coating layer from which they gradually diffuse into the layer of stoving lacquer to be protected. The adjacent surface-coating layer may be a primer under the stoving lacquer or a finishing lacquer over the stoving lacquer.

It is also possible to add to the resin, for example, photosensitisers which shift or increase the spectral sensitivity so that the irradiation period can be reduced and/or other light sources can be used. Examples of photosensitisers are aromatic ketones or aromatic aldehydes (as described, for example, in U.S. Pat. No. 4,017,652), 3-acyl-coumarins (as described, for example, in U.S. Pat. No. 4,366,228, EP 738928, EP 22188), keto-coumarines (as described e.g. in U.S. Pat. No. 5,534,633, EP 538997, JP 8272095-A), styryl-coumarines (as described e.g. in EP 624580), 3-(aroylmethylene)-thiazolines, thioxanthones, condensed aromatic compounds, such as perylene, aromatic amines (as described, for example, in U.S. Pat. No. 4,069, 954 or WO 96/41237) or cationic and basic colourants (as described, for example, in U.S. Pat. No. 4,026,705), for example eosine, rhodanine and erythrosine colourants, as well as dyes and pigments as described for example in JP 8320551-A, EP 747771, JP 7036179-A, EP 619520, JP 6161109-A, JP 6043641, JP 6035198-A, WO 93/15440, EP 568993, JP 5005005-A, JP 5027432-A, JP 5301910-A, JP 4014083-A, JP 4294148-A, EP 359431, EP 103294, U.S. Pat. No. 4,282,309, EP 39025, EP 5274, EP 727713, EP 726497 or DE 2027467.

Other customary additives are—depending on the intended use—optical brighteners, fillers, pigments, colourants, wetting agents or flow improvers and adhesion promoters.

For curing thick and pigmented coatings, the addition of micro glass beads or powdered glass fibres, as described in U.S. Pat. No. 5,013,768, is suitable.

Oxime derivatives can also be used, for example, in hybrid systems. These systems are based on formulations that are fully cured by two different reaction mechanisms. Examples thereof are systems that comprise components that are capable of undergoing an acid-catalysed crosslinking reaction or polymerisation reaction, but that also comprise further components that crosslink by a second mechanism. Examples of the second mechanism are radical full cure, oxidative crosslinking or humidity-initiated crosslinking. The second curing mechanism may be initiated purely thermally, if necessary with a suitable catalyst, or also by means of light using a second photoinitiator. Suitable additional photoinitiators are described above.

If the composition comprises a radically crosslinkable component, the curing process, especially of compositions that are pigmented (for example with titanium dioxide), can also be assisted by the addition of a component that is radical-forming under thermal conditions, such as an azo compound, for example 2,2'-azobis(4-methoxy-2,4-dimethylvaleronitrile), a triazene, a diazosulfide, a pentazadiene or a peroxy compound, such as, for example, a hydroperoxide or peroxycarbonate, for example tert-butyl hydroperoxide, as described, for example, in EP 245639. The addition of redox initiators, such as cobalt salts, enables the curing to be assisted by oxidative crosslinking with oxygen from the air.

The surface coating can be applied by one of the methods customary in the art, for example by spraying, painting or immersion. When suitable surface coatings are used, electrical application, for example by anodic electrophoretic deposition, is also possible. After drying, the surface coating film is irradiated. If necessary, the surface coating film is then fully cured by means of heat treatment.

The compounds of formulae I or II can also be used for curing mouldings made from composites. A composite consists of a self-supporting matrix material, for example a glass fibre fabric, impregnated with the photocuring formulation.

It is known from EP 592139 that oxime derivatives can be used as acid generators, which can be activated by light in compositions that are suitable for the surface treatment and cleaning of glass, aluminium and steel surfaces. The use of such compounds in organosilane systems results in compositions that have significantly better storage stability than those obtained when the free acid is used. The compounds of formula I or II are also suitable for this application.

The oxime derivatives of the present invention can also be used to shape polymers that undergo an acid induced transition into a state where they have the required properties using photolithography. For instance the oxime derivatives can be used to pattern conjugated emissive polymers as described, for example, in M. L. Renak; C. Bazan; D. Roitman; Advanced materials 1997, 9, 392. Such patterned emissive polymers can be used to manufacture microscalar patterned Light Emitting Diodes (LED) which can be used to manufacture displays and data storage media. In a similar way precursors for polyimides (e.g. polyimid precursors with acid labile protecting groups that change solubility in the developer) can be irradiated to form patterned polyimide layers which can serve as protective coatings, insulating layers and buffer layers in the production of microchips and printed circuit boards.

The formulations of the invention may also be used as conformal coatings, photoimagable insulating layers and dielectrics as they are used in sequential build up systems for printed circuit boards, stress buffer layers in the manufacturing of integrated circuits.

It is known that conjugated polymers like, e.g. polyanilines can be converted from semiconductive to conductive state by means of proton doping. The oxime derivatives of the present invention can also be used to imagewise irradiate compositions comprising such conjugated polymers in order to form conducting structures (exposed areas) embedded in insulating material (non exposed areas). These materials can be used as wiring and connecting parts for the production of electric and electronic devices.

Suitable radiation sources for the compositions comprising compounds of formula I or II are radiation sources that emit radiation of a wavelength of approximately from 150 to 1500, for example from 180 to 1000, or preferably from 190 to 700 nanometers as well as e-beam radiation and high-energy electromagnetic radiation such as X-rays. Both, point sources and planiform projectors (lamp carpets) are suitable. Examples are: carbon arc lamps, xenon arc lamps, medium pressure, high pressure and low pressure mercury lamps, optionally doped with metal halides (metal halide lamps), microwave-excited metal vapour lamps, excimer lamps, superactinic fluorescent tubes, fluorescent lamps, argon filament lamps, electronic flash lamps, photographic flood lights, electron beams and X-ray beams generated by means of synchrotrons or laser plasma. The distance between the radiation source and the substrate according to the invention to be irradiated can vary, for example, from 2 cm to 150 cm, according to the intended use and the type and/or strength of the radiation source. Suitable radiaiton sources are especially mercury vapour lamps, especially medium and high pressure mercury lamps, from the radiation of which emission lines at other wavelengths can, if desired, be filtered out. That is especially the case for relatively short wavelength radiation. It is, however, also possible to use low energy lamps (for example fluorescent tubes) that are capable of emitting in the appropriate wavelength range. An example thereof is the Philips TL03 lamp. Another type of radiation source that can be used are the light emitting diodes (LED) that emitt at different wavelengths throughout the whole spectrum either as small band emitting source or as broad band (white light) source. Also suitable are laser radiation sources, for example excimer lasers, such as Kr—F lasers for irradiation at 248 nm, Ar—F lasers at 193 nm, or $F_2$ laser at 157 nm. Lasers in the visible range and in the infrared range can also be used. Especially suitable is radiation of the mercury i, h and g lines at wavelengths of 365, 405 and 436 nanometers. A suitable laser-beam source is, for example, the argon-ion laser, which emits radiation at wavelengths of 454, 458, 466, 472, 478, 488 and 514 nanometers. Nd-YAG-lasers emitting light at 1064 nm and its second and third harmonic (532 nm and 355 nm respectively) can also be used. Also suitable is, for example, a helium/cadmium laser having an emission at 442 nm or lasers that emit in the UV range. With that type of irradiation, it is not absolutely essential to use a photomask in contact with the photopolymeric coating to produce a positive or negative resist; the controlled laser beam is capable of writing directly onto the coating. For that purpose the high sensitivity of the materials according to the invention is very advantageous, allowing high writing speeds at relatively low intensities. On irradiation, the oxime derivatives in the composition in the irradiated sections of the surface coating decompose to form the acids.

In contrast to customary UV curing with high-intensity radiation, with the compounds according to the invention activation is achieved under the action of radiation of relatively low intensity. Such radiation includes, for example, daylight (sunlight), and radiation sources equivalent to daylight. Sunlight differs in spectral composition and intensity from the light of the artificial radiation sources customarily used in UV curing. The absorption characteristics of the compounds according to the invention are as well suitable for exploiting sunlight as a natural source of radiation for curing. Daylight-equivalent artificial light sources that can be used to activate the compounds according to the invention are to be understood as being projectors of low intensity, such as certain fluorescent lamps, for example the Philips TL05 special fluorescent lamp or the Philips TL09 special fluorescent lamp. Lamps having a high daylight content and daylight itself are especially capable of curing the surface of a surface-coating layer satisfactorily in a tack-free manner. In that case expensive curing apparatus is superfluous and the compositions can be used especially for exterior finishes. Curing with daylight or daylight-equivalent light sources is an energy-saving method and prevents emissions of volatile organic components in exterior applications. In contrast to the conveyor belt method, which is suitable for flat components, daylight curing can also be used for exterior finishes on static or fixed articles and structures.

The surface coating to be cured can be exposed directly to sunlight or daylight-equivalent light sources. The curing can, however, also take place behind a transparent layer (e.g. a pane of glass or a sheet of plastics).

The examples which follow illustrate the invention in more detail. Parts and percentages are, as in the remainder of the description and in the claims, by weight, unless stated otherwise. Where alkyl radicals having more than three carbon atoms are referred to without any mention of specific isomers, the n-isomers are meant in each case.

EXAMPLE 1

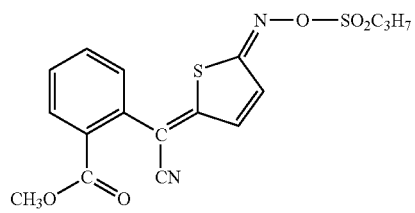

($R_1$=methoxy; A=S; $R_6$=propylsulfonyl; $R_2$, $R_3$, $R_4$, $R_5$, $R_7$, $R_8$=hydrogen)

1.1: 2-[Cyano-(5-hydroxyimino-5H-thiophen-2-ylidene)-methyl]-benzoic acid methyl ester To sodium methoxide (79.8 mmol) in 40 mL of methanol are successively added methyl 2-cyanomethylbenzoate (4.0 g, 22.8 mmol) in toluene (7 mL) and 2-nitrothiophene (22.8 mmol) in toluene (10 mL) at 0° C. After stirring for 1.5 h at the same temperature, the reaction mixture is poured into water and neutralized with acetic acid. The crude product is extracted with ethyl acetate three times, washed with water twice, and dried over MgSO$_4$. After the MgSO$_4$ is filtered off, the filtrate is concentrated under reduced pressure. The residue is purified by column chromatography on silica gel with hexane and ethyl acetate (1:1) as eluent, yielding 6.5 g of the product as an isomeric mixture. The product is further purified by recrystallization from toluene to afford 2.0 g of the product, which is a yellow solid, as a single isomer. The structure is confirmed by the $^1$H-NMR spectrum (CDCl$_3$). δ [ppm]: 3.91 (s, 3H), 6.06 (d, 1H), 6.86 (d, 1H), 7.37 (dd, 1H), 7.53 (ddd, 1H), 7.61 (ddd, 1H), 8.10 (dd, 1H), 8.93 (bs, 1H).

1.2: 2-[Cyano-(5-n-propanesulfonyloxyimino-5H-thiophen-2-ylidene)-methyl]-benzoic acid methyl ester To the oxime prepared according to example 1.1 (2.0 g, 7.0 mmol) in 10 mL of tetrahydrofuran (THF) are successively added 1-propanesulfonyl chloride (0.87 mL, 7.7 mmol) and triethylamine (1.5 mL, 10.5 mmol) at 0° C. After stirring for 2.5 h at the same temperature, the reaction mixture is poured into water. The crude product is extracted with ethyl acetate twice, washed with 3% sulfuric acid twice and water three times, and dried over MgSO$_4$. After the MgSO$_4$ is filtered off, the filtrate is concentrated under reduced pressure. The residue is purified by column chromatography on silica gel with hexane and ethyl acetate (4:1 to 1:1) as eluent, yielding 1.57 g of the product as a yellow solid with a melting point (mp.) of 110–112° C. The structure is confirmed by the $^1$H-NMR spectrum (CDCl$_3$). δ [ppm]: 1.14 (t, 3H), 2.00 (tq, 2H), 3.63 (t, 2H), 3.92 (s, 3H), 6.11 (d, 1H), 6.81 (d, 1H), 7.37 (dd, 1H), 7.58 (ddd, 1H), 7.65 (ddd, 1H), 8.14 (dd, 1H).

EXAMPLE 2

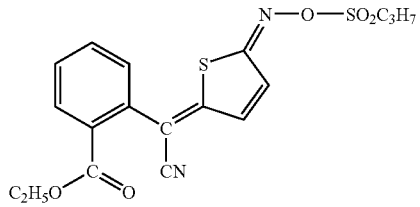

(R$_1$=ethoxy; A=S; R$_6$=propylsulfonyl; R$_2$, R$_3$, R$_4$, R$_5$, R$_7$, R$_8$=hydrogen)

2.1: 2-[Cyano-(5-hydroxyimino-5H-thiophen-2-ylidene)-methyl]-benzoic acid ethyl ester To sodium ethoxide (5.43 g, 79.8 mmol) in 40 mL of ethanol are successively added methyl 2-cyanomethylbenzoate (4.0 g, 22.8 mmol) in toluene (7 mL) and 2-nitrothiophene (22.8 mmol) in toluene (10 mL) at 0° C. After stirring for 1.5 h at the same temperature, the reaction mixture is poured into water and neutralized with acetic acid. The crude product is extracted with ethyl acetate twice, washed with water twice, and dried over MgSO$_4$. After the MgSO$_4$ is filtered off, the filtrate is concentrated under reduced pressure. The residue is purified by column chromatography on silica gel with hexane and ethyl acetate (1:1) as eluent, yielding 5.1 g of the product as an isomeric mixture. The product is further purified by recrystallization from toluene to afford 2.4 g of the product, which is a yellow solid, as a single isomer. The structure is confirmed by the $^1$H-NMR spectrum (CDCl$_3$). δ [ppm]: 1.35 (t, 3H), 4.35 (q, 2H), 6.05 (d, 1H), 6.85 (d, 1H), 7.37 (dd, 1H), 7.53 (ddd, 1H), 7.60 (ddd, 1H), 8.10 (dd, 1H), 8.77 (bs, 1H).

2.2: 2-[Cyano-(5-n-propanesulfonyloxyimino-5H-thiophen-2-ylidene)-methyl]-benzoic acid ethyl ester The product is prepared from the oxime achieved according to example 2.1 under the same condition as described in example 1.2. The structure is confirmed by the $^1$H-NMR spectrum (CDCl$_3$). δ [ppm]: 1.13 (t, 3H), 1.37 (t, 3H), 1.99 (tq, 2H), 3.63 (t, 2H), 4.37 (q, 2H), 6.11 (d, 1H), 6.81 (d, 1H), 7.36 (dd, 1H), 7.58 (ddd, 1H), 7.65 (ddd, 1H), 8.15 (dd, 1H).

EXAMPLE 3

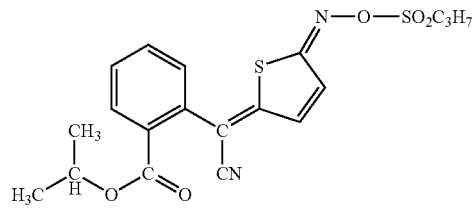

(R$_1$=isoproyloxy; A=S; R$_6$=propylsulfonyl; R$_2$, R$_3$, R$_4$, R$_5$, R$_7$, R$_8$=hydrogen)

3.1: 2-[Cyano-(5-hydroxyimino-5H-thiophen-2-ylidene)-methyl]-benzoic acid isopropyl ester To sodium isopropoxide (160 mmol) in 140 mL of isopropyl alcohol and 140 mL of toluene are added methyl 2-cyanomethylbenzoate (8.0 g, 45.7 mmol) and 2-nitrothiophene (45.7 mmol) in toluene (25 mL) at 0° C. After stirring for 5 h at the same temperature, the reaction mixture is poured into water and neutralized with acetic acid. The crude product is extracted with ethyl acetate twice, washed with water twice, and dried over MgSO$_4$. After the MgSO$_4$ is filtered off, the filtrate is concentrated under reduced pressure. The residue is purified by column chromatography on silica gel with hexane and ethyl acetate (1:1) as eluent, yielding 12.3 g of the product as an isomeric mixture. The product is further purified by recrystallization from toluene to afford 2.97 g of the product, which is a yellow solid, as a single isomer. The structure is confirmed by the $^1$H-NMR spectrum (DMSO-d$_6$). δ [ppm]: 1.21 (d, 6H), 5.04 (sept, 1H), 5.98 (d, 1H), 7.31 (d, 1H), 7.52 (dd, 1H), 7.62 (ddd, 1H), 7.72 (ddd, 1H), 7.96 (dd, 1H). The hydrogen of N—OH is not observed.

3.2: 2-[Cyano-(5-n-propanesulfonyloxyimino-5H-thiophen-2-ylidene)-methyl]-benzoic acid isopropyl ester The product is prepared from the oxime as achieved in example 3.1 under the same condition as described in example 1.2. The structure is confirmed by the $^1$H-NMR spectrum (CDCl$_3$). δ [ppm]: 1.13 (t, 3H), 1.33 (bs, 6H), 1.99 (tq, 2H), 3.63 (t, 2H), 5.22 (sept, 1H), 6.09 (d, 1H), 6.81 (d, 1H), 7.35 (dd, 1H), 7.58 (ddd, 1H), 7.63 (ddd, 1H), 8.13 (dd, 1H). m.p. 117–118° C.

EXAMPLES 4–6, 7.1, 7.2, 8.1 AND 8.2

The compounds of examples 4–6, 7.1, 7.2, 8.1 and 8.2 are prepared according to the methods described in examples 1 and 2 with the corresponding reagents. The compounds, their melting point, and $^1$H NMR data are given in table 1.

TABLE 1

| example | $R_1$ | $R_6$ | mp [° C.] $^1$HNMR (CDCl$_3$): δ [ppm] |
|---|---|---|---|
| 4 | —OCH$_3$ | —SO$_2$C$_6$H$_4$CH$_3$-p | 177<br>2.45(s, 3H), 3.87(s, 3H), 6.02(d, 1H), 6.75 (d, 1H), 7.31(dd, 1H), 7.38(d, 2H), 7.55 (ddd, 1H), 7.62(ddd, 1H), 8.09–8.12(m, 3H) |
| 5 | —OCH$_3$ | camphorsulfonyl | 165–168<br>0.94(s, 3H), 1.16(s, 3H), 1.43–1.50(m, 1H), 1.82–1.90(m, 1H), 1.97(d, 1H), 2.04–2.16 (m, 2H), 2.37–2.51(m, 2H), 3.84(d, 1H), 3.91(s, 3H), 3.92(d, 1H), 6.12(d, 1H), 6.81 (d, 1H), 7.37(dd, 1H), 7.57(ddd, 1H), 7.64 (ddd, 1H), 8.13(dd, 1H) |
| 6 | —OCH$_3$ | —SO$_2^n$C$_8$H$_{17}$ | 71–82<br>0.87(t, 3H), 1.21–1.40(m, 8H), 1.45–1.54(m, 2H), 1.91–1.99(m, 2H), 3.64(t, 2H), 3.92(s, 3H), 6.11(d, 1H), 6.81(d, 1H), 7.36(d, 1H), 7.58(dd, 1H), 7.65(dd, 1H), 8.14(d, 1H) |
| 7.1 | —O$^n$CH$_4$H$_9$ | H | 133–134<br>0.93(t, 3H), 1.40(tq, 2H), 1.66–1.73(m, 2H), 4.30(t, 2H), 6.05(d, 1H), 6.86(d, 1H), 7.37 (dd, 1H), 7.53(ddd, 1H), 7.60(ddd, 1H), 8.10(dd, 1H), 9.39(bs, 1H) |
| 7.2 | —O$^n$CH$_4$H$_9$ | —SO$_2$C$_6$H$_4$CH$_3$-p | 119–121<br>0.84(t, 3H), 1.28(tq, 2H), 1.58(tt, 2H), 2.45 (s, 3H), 4.24(bs, 2H), 6.02(d, 1H), 6.75(d, 1H), 7.30(dd, 1H), 7.38(d, 2H), 7.55(ddd, 1H), 7.61(ddd, 1H), 8.09–5.13(m, 3H) |
| 8.1 | —O—CH(C$_2$H$_5$)—CH$_3$ | H | 151<br>0.79–0.99(m, 3H), 1.17–1.41(m, 3H), 1.54–1.78(m, 2H), 5.06(q, 1H), 6.02(d, 1H), 6.85 (d, 1H), 7.36(d, 1H), 7.49–7.62(m, 2H), 8.03–8.14(m, 1H), 9.68(broad s, 1H) |
| 8.2 | —O—CH(C$_2$H$_5$)—CH$_3$ | —SO$_2$C$_6$H$_4$CH$_3$-p | 134<br>0.68–0.94(m, 3H), 1.08–1.31(m, 3H), 1.35–1.73(m, 2H), 2.45(s, 3H), 4.95–5.03(m, 1H), 5.97(d, 1H), 6.74(d, 1H), 7.29(d, 1H), 7.37(d, 2H), 7.55(ddd, 1H), 7.60(ddd, 1H), 8.07–8.16(m, 3H) |

EXAMPLE 9

A chemically amplified positive resist formulation is prepared by mixing the following components:
100.00 parts of a resin binder (a copolymer of 22 mol-% of styrene, 69 mol-% of p-hydroxystyrene and 9 mol-% of t-butyl acrylate, having a Mw of 9850; $^{RTM}$Maruzen MARUKA LYNCUR PHS/STY/TBA, provided by Maruzen Oil Company, Japan)
0.48 parts of a levelling agent (FC-430, provided by 3M)
475.00 parts of propylene glycol methyl ether acetate (PGMEA) (provided by Tokyo Kasei, Japan)
4.00 parts of the photoacid generator to be tested The resist formulation is spin coated onto a hexamethyl dimethylsilazane-treated silicone wafer at 3000 rpm for 45 seconds and softbaked for 90 seconds at 140° C. on a hotplate to obtain a film thickness of 800 nm. The resist film is then exposed to deep UV radiation of 254 nm wavelength through a narrow band interference filter and a multidensity quartz mask using an Ushio's high pressure mercury lamp, UXM-501 MD, and a mask aligner Canon PLA-521. The samples then are post exposure baked for 90 seconds at 140° C. on a hotplate and developed. The exposure intensity is measured with a Unimeter UIT-150 from Ushio. The Dose to Clear ($E_0$), which is the dose just sufficient to completely remove the resist film with 60 seconds immersion development in 1.79% aqueous tetramethyl ammonium hydroxide developer is determined from the measured contrast curve. The smaller the required dose the more sensitive is the resist formulation. The results are collected in Table 2 and demonstrate that the compositions are suitable for the preparation of positive photoresists.

TABLE 2

| Compound of example | Dose to Clear ($E_0$) [mJ/cm$^2$] |
|---|---|
| 1 | 1.38 |
| 2 | 1.56 |
| 3 | 1.27 |
| 5 | 2.88 |

EXAMPLE 10

The degradation point (td) of the photolatent acid generator compound in the presence of the same amount (with respect to the weight) of poly(4-hydroxystyrene), which has a Mw of 5100 and is commercially available under the trade name of $^{RTM}$Maruzene MARUKA LYNCUR PHMC from Maruzene Oil Company of Tokyo, Japan, is determined by DSC analysis (Differential Scanning Calorimetry). The higher the values, the more thermostable are the tested photolatent acid compounds. The results are summarized in the table 2 below.

TABLE 2

| Compound of example | Td (° C.) |
|---|---|
| 1 | 151 |
| 2 | 155 |
| 3 | 158 |
| 4 | 188 |
| 5 | 186 |
| 6 | 142 |
| 7.2 | 163 |
| 8.2 | 163 |

EXAMPLE 11

A chemically amplified positive resist formulation is prepared by mixing the following components:
100.0 parts of a resin binder (a copolymer of 38 mol % p-(2-ethoxyethyloxy)styrene, and 62 mol % p-hydroxystyrene, derived from VP-8000 having a Mw of 11900, provided by Nippon Soda Co., Ltd, Japan)
0.5 parts of a leveling agent (FC-430, provided by 3M)
475.0 parts of propylene glycol methyl ether acetate (PGMEA) (provided by Tokyo Kasei, Japan)
4.0 parts of the compound of example 5 as the photoacid generator to be tested The resist formulation is spin coated onto a hexamethyldisilazane-treated silicone wafer at 1710 rpm for 45 seconds and softbaked for 60 seconds at 110° C. on a hotplate to obtain a film thickness of 785 nm. The resist film is then exposed with the same manner as described in Example 9. After a post exposure bake for 60 seconds at 110° C. on a hotplate the resist is developed. The exposure intensity is measured with Unimeter UIT-150 from Ushio. The $E_0$, which is the dose just sufficient to completely remove the resist film with 60 seconds immersion development in 2.38% aqueous tetramethylammonium hydroxide developer, is determined from the measured contrast curve (characteristic curve). The result is that $E_0$ is 0.083 mJ/cm² which demonstrates that the compositions are suitable for the preparation of positive photoresists.

What is claimed is:

1. A compound of the formula I or II

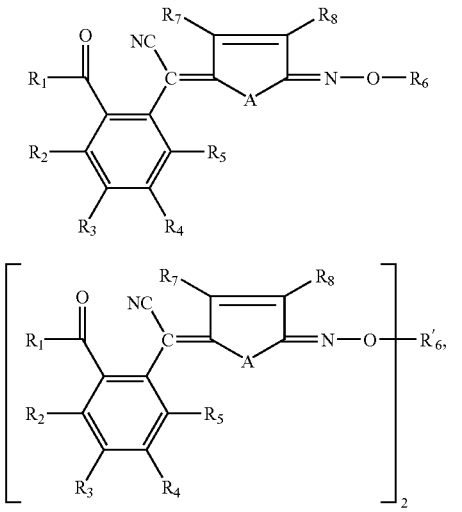

wherein
$R_1$ is $C_1$–$C_{12}$alkyl, $C_1$–$C_4$haloalkyl, hydrogen, $OR_9$, $NR_{10}R_{11}$, $SR_{12}$ or is phenyl which is unsubstituted or substituted by OH, $C_1$–$C_{18}$alkyl, halogen and/or $C_1$–$C_{12}$alkoxy;

$R_2$, $R_3$, $R_4$ and $R_5$ are independently of each other hydrogen, $C_1$–$C_{12}$alkyl, $C_1$–$C_4$haloalkyl, halogen, phenyl, $OR_{13}$, $NR_{14}R_{15}$, $SR_{16}$, CN, $NO_2$, $C_2$–$C_6$alkanoyl, benzoyl, —(CO)$OR_9$, —(CO)$NR_{10}R_{11}$ or —(CO)$SR_{12}$;

$R_6$ is $C_1$–$C_{18}$alkylsulfonyl, $C_1$–$C_{10}$haloalkylsulfonyl, camphorylsulfonyl, phenyl-$C_1$–$C_3$alkylsulfonyl, $C_3$–$C_{30}$cycloalkylsulfonyl, phenylsulfonyl, naphthylsulfonyl, anthracylsulfonyl or phenanthrylsulfonyl, wherein the groups cycloalkyl, phenyl, naphthyl, anthracyl and phenanthryl of the radicals $C_3$–$C_{30}$cycloalkylsulfonyl, phenyl-$C_1$–$C_3$alkylsulfonyl, phenylsulfonyl, naphthylsulfonyl, anthracylsulfonyl and phenanthrylsulfonyl are unsubstituted or substituted by one or more halogen, $C_1$–$C_4$haloalkyl, CN, $NO_2$, $C_1$–$C_{16}$alkyl, phenyl, $C_1$–$C_4$alkylthio, $OR_{13}$, (CO)$OR_9$, $C_1$–$C_4$alkyl-(CO)O—, $R_9OSO_2$— and/or —$NR_{14}R_{15}$; or $R_6$ is $C_2$–$C_6$haloalkanoyl, halobenzoyl; or $R_6$ is a group

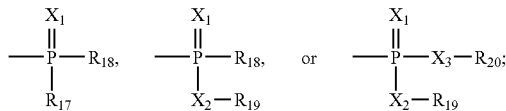

$X_1$, $X_2$ and $X_3$ independently of each other are O or S;
$R'_6$ is phenylenedisulfonyl, naphthylenedisulfonyl,

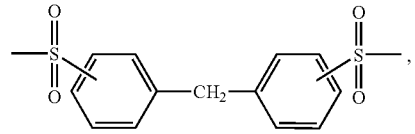

diphenylenedisulfonyl, or oxydiphenylenedisulfonyl, wherein these radicals are unsubstituted or substituted by $C_1$–$C_{12}$alkyl; or $R_{16}$ is $C_2$–$C_{12}$alkylenedisulfonyl;

$R_7$ and $R_8$ are independently of each other hydrogen, halogen, $C_1$–$C_6$alkyl, $C_1$–$C_6$alkoxy, $C_1$–$C_4$haloalkyl, CN, $NO_2$, $C_2$–$C_6$alkanoyl, benzoyl, phenyl, —S-phenyl, $OR_{13}$, $SR_{16}$, $NR_{14}R_{15}$, $C_2$–$C_6$alkoxycarbonyl, phenoxycarbonyl, $S(O)_n C_1$–$C_6$alkyl, $S(O)_n$—$C_6$–$C_{12}$aryl, $C_1$–$C_{12}$alkyl-substituted $S(O)_n$—$C_6$–$C_{12}$aryl, $SO_2O$—$C_1$–$C_6$alkyl, $SO_2O$—$C_6$–$C_{10}$aryl or $NHCONH_2$;

n is 0, 1 or 2;

$R_9$ is hydrogen, $C_1$–$C_{18}$alkyl which is unsubstituted or substituted by phenyl, OH, $C_1$–$C_{12}$alkoxy, $C_2$–$C_{12}$alkoxycarbonyl, phenoxy, phenoxycarbonyl, phenylthio, phenylthiocarbonyl, $NR_{14}R_{15}$, $C_1$–$C_{12}$alkylsulfonyl, phenylsulfonyl, (4-methylphenyl)sulfonyl and/or by $C_2$–$C_6$alkanoyl; or $R_9$ is $C_2$–$C_{18}$alkyl which is interrupted by one or more —O—, and which is unsubstituted or substituted by phenyl, OH, $C_1$–$C_{12}$alkoxy, $C_2$–$C_{12}$alkoxycarbonyl, phenoxy, phenoxycarbonyl, phenylthio, phenylthiocarbonyl, $NR_{14}R_{15}$, $C_1$–$C_{12}$alkylsulfonyl, phenylsulfonyl, (4-methylphenyl)sulfonyl and/or by $C_2$–$C_6$alkanoyl; or $R_9$ is phenyl which is unsubstituted or substituted by OH, $C_1$–$C_{18}$alkyl, halogen and/or $C_1$–$C_{12}$alkoxy;

$R_{10}$, $R_{11}$, $R_{14}$ and $R_{15}$ independently of each other are hydrogen or $C_1$–$C_{18}$alkyl which is unsubstituted or substituted by OH, $C_1$–$C_4$alkoxy, $C_2$–$C_{12}$alkoxycarbonyl, phenoxy, phenoxycarbonyl, phenylthio, phenylthiocarbonyl, phenylamino, phenylaminocarbonyl, $C_1$–$C_{12}$alkylsulfonyl, phenylsulfonyl, (4-methylphenyl)sulfonyl and/or $C_2$–$C_6$alkanoyl; or $R_{10}$, $R_{11}$, $R_{14}$ and $R_{15}$ are $C_2$–$C_{18}$alkyl which is interrupted by one or more —O—, and which is unsubstituted or substituted by OH, $C_1$–$C_4$alkoxy, $C_2$–$C_{12}$alkoxycarbonyl, phenoxy, phenoxycarbonyl, phenylthio, phenylthiocarbonyl, phenylamino, phenylaminocarbonyl, $C_1$–$C_{12}$alkylsulfonyl, phenylsulfonyl, (4-methylphenyl)sulfonyl and/or $C_2$–$C_6$alkanoyl; or $R_{10}$ and $R_{11}$ are phenyl which is unsubstituted or substituted by OH, $C_1$–$C_{18}$alkyl, halogen and/or $C_1$–$C_{12}$alkoxy; or $R_{10}$, $R_{11}$, $R_{14}$ and $R_{15}$ are $C_2$–$C_{18}$alkanoyl, which is unsubstituted or substituted by phenyl, OH, $C_1$–$C_{12}$alkoxy, $C_2$–$C_{12}$alkoxycarbonyl, phenoxy, phenoxycarbonyl, phenylthio, phenylthiocarbonyl, phenylamino, phenylaminocarbonyl, $C_1$–$C_{12}$alkylsulfonyl, phenylsulfonyl, (4-methylphenyl)sulfonyl, and/or by $C_2$–$C_6$alkanoyl; or $R_{10}$, $R_{11}$, $R_{14}$ and $R_{15}$ are $C_1$–$C_{18}$alkylsulfonyl which is unsubstituted or substituted by phenyl, OH, $C_1$–$C_{12}$alkoxy, $C_2$–$C_{12}$alkoxycarbonyl, phenoxy, phenoxycarbonyl, phenylthio, phenylthiocarbonyl, phenylamino, phenylaminocarbonyl, $C_1$–$C_{12}$alkylsulfonyl, phenylsulfonyl, (4-methylphenyl)sulfonyl, and/or by $C_2$–$C_6$alkanoyl; or $R_{10}$, $R_{11}$, $R_{14}$ and $R_{15}$ are phenylsulfonyl which is unsubstituted or substituted by one or more halogen, $C_1$–$C_4$haloalkyl, CN, $NO_2$, $C_1$–$C_{16}$alkyl, phenyl, $C_1$–$C_4$alkylthio, $C_1$–$C_{12}$alkoxy and/or phenoxy; or $R_{10}$, $R_{11}$, $R_{14}$ and $R_{15}$ are benzoyl, $C_1$–$C_{10}$haloalkylsulfonyl, camphorylsulfonyl, phenyl-$C_1$–$C_3$alkylsulfonyl, $C_3$–$C_{30}$cycloalkylsulfonyl, naphthylsulfonyl, anthracylsulfonyl or phenanthrylsulfonyl; or $R_{10}$ and $R_{11}$, or $R_{14}$ and $R_{15}$ together with the nitrogen atom to which they are attached, form a 5-, 6- or 7-membered ring which optionally is interrupted by —O— or by —$NR_{13}$—;

$R_{12}$ is hydrogen, phenyl, $C_1$–$C_{18}$alkyl which is unsubstituted or substituted by phenyl, OH, $C_1$–$C_{12}$alkoxy, $C_2$–$C_{12}$alkoxycarbonyl, phenoxy, phenoxycarbonyl, phenylthio, phenylthiocarbonyl, $NR_{14}R_{15}$, $C_1$–$C_{12}$alkylsulfonyl, phenylsulfonyl, (4-methylphenyl)sulfonyl, and/or by $C_2$–$C_6$alkanoyl; or $R_{12}$ is $C_2$–$C_{18}$alkyl which is interrupted by one or more —O— and which is unsubstituted or substituted by phenyl, OH, $C_1$–$C_{12}$alkoxy, $C_2$–$C_{12}$alkoxycarbonyl, phenoxy, phenoxycarbonyl, phenylthio, phenylthiocarbonyl, $NR_{14}R_{15}$, $C_1$–$C_{12}$alkylsulfonyl, phenylsulfonyl, (4-methylphenyl)sulfonyl, and/or by $C_2$–$C_6$alkanoyl;

$R_{13}$ has one of the meanings given for $R_9$ or is $C_2$–$C_{18}$alkanoyl which is unsubstituted or substituted by phenyl, OH, $C_1$–$C_{12}$alkoxy, $C_2$–$C_{12}$alkoxycarbonyl, phenoxy, phenoxycarbonyl, phenylthio, phenylthiocarbonyl, $NR_{14}R_{15}$, $C_1$–$C_{12}$alkylsulfonyl, phenylsulfonyl, (4-methylphenyl)sulfonyl, and/or by $C_2$–$C_6$alkanoyl; or $R_{13}$ is $C_1$–$C_{18}$alkylsulfonyl which is unsubstituted or substituted by phenyl, OH, $C_1$–$C_{12}$alkoxy, $C_2$–$C_{12}$alkoxycarbonyl, phenoxy, phenoxycarbonyl, phenylthio, phenylthiocarbonyl, $NR_{14}R_{15}$, $C_1$–$C_{12}$alkylsulfonyl, phenylsulfonyl, (4-methylphenyl)sulfonyl, and/or by $C_2$–$C_6$alkanoyl; or $R_{13}$ is phenylsulfonyl which is unsubstituted or substituted by one or more halogen, $C_1$–$C_4$haloalkyl, CN, $NO_2$, $C_1$–$C_{16}$alkyl, phenyl, $C_1$–$C_4$alkylthio, $C_1$–$C_{12}$alkoxy and/or phenoxy; or $R_{13}$ is benzoyl, $C_1$–$C_{10}$haloalkylsulfonyl, camphorylsulfonyl, phenyl-$C_1$–$C_3$alkylsulfonyl, $C_3$–$C_{30}$cycloalkylsulfonyl, naphthylsulfonyl, anthracylsulfonyl or phenanthrylsulfonyl;

$R_{16}$ has one of the meanings given for $R_{12}$ or is $C_2$–$C_{18}$alkanoyl which is unsubstituted or substituted by phenyl, OH, $C_1$–$C_{12}$alkoxy, $C_2$–$C_{12}$alkoxycarbonyl, phenoxy, phenoxycarbonyl, phenylthio, phenylthiocarbonyl, $NR_{14}R_{15}$, $C_1$–$C_{12}$alkylsulfonyl, phenylsulfonyl, (4-methylphenyl)sulfonyl, and/or by $C_2$–$C_6$alkanoyl; or $R_{16}$ is $C_1$–$C_{18}$alkylsulfonyl which is unsubstituted or substituted by phenyl, OH, $C_1$–$C_{12}$alkoxy, $C_2$–$C_{12}$alkoxycarbonyl, phenoxy, phenoxycarbonyl, phenylthio, phenylthiocarbonyl, $NR_{14}R_{15}$, $C_1$–$C_{12}$alkylsulfonyl, phenylsulfonyl, (4-methylphenyl)sulfonyl, and/or by $C_2$–$C_6$alkanoyl; or $R_{16}$ is phenylsulfonyl which is unsubstituted or substituted by one or more halogen, $C_1$–$C_4$haloalkyl, CN, $NO_2$, $C_1$–$C_{16}$alkyl, phenyl, $C_1$–$C_4$alkylthio, $C_1$–$C_{12}$alkoxy and/or phenoxy; or $R_{16}$ is benzoyl, $C_1$–$C_{10}$haloalkylsulfonyl, camphorylsulfonyl, phenyl-$C_1$–$C_3$alkylsulfonyl, $C_3$–$C_{30}$cycloalkylsulfonyl, naphthylsulfonyl, anthracylsulfonyl or phenanthrylsulfonyl;

$R_{17}$, $R_{18}$, $R_{19}$ and $R_{20}$ independently of one another are $C_1$–$C_6$alkyl which is unsubstituted or substituted by halogen; or $R_{17}$, $R_{18}$, $R_{19}$ and $R_{20}$ are phenyl which is unsubstituted or substituted by $C_1$–$C_4$alkyl or halogen; or $R_{19}$ and $R_{20}$ together are 1,2-phenylene or $C_2$–$C_6$alkylene which is unsubstituted or substituted by $C_1$–$C_4$alkyl or halogen;

A is S, O, $NR_{13}$, or a group of formula A1, A2 or A3

(A₁)

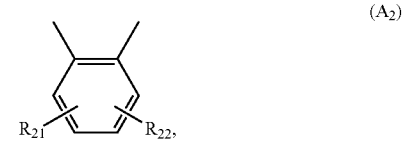

(A₂)

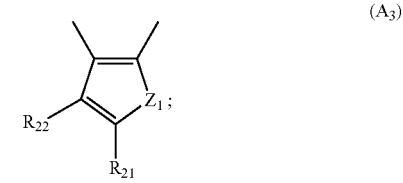

(A₃)

$R_{21}$ and $R_{22}$ independently of one other have one of the meanings given for $R_7$, or $R_{21}$ and $R_{22}$ together are —CO—$NR_{13}$CO—, or $R_{21}$ and $R_{22}$ together are —C($R_{23}$)=C($R_{24}$)—C($R_{25}$)=C($R_{26}$)—;

$R_{23}$, $R_{24}$, $R_{25}$ and $R_{26}$ independently of one another are hydrogen, $C_1$–$C_4$alkyl, halogen, phenyl, $OR_{13}$, $SR_{16}$, $NR_{14}R_{15}$, —S-phenyl, $C_2$–$C_6$alkoxycarbonyl, phenoxycarbonyl, CN, $NO_2$, $C_1$–$C_4$haloalkyl, $S(O)_n$$C_1$–$C_6$alkyl, $S(O)_n$—$C_6$–$C_{12}$aryl, $C_1$–$C_{12}$alkyl-substituted $S(O)_n$—$C_6$–$C_{12}$aryl, $SO_2O$—$C_1$–$C_6$alkyl, $SO_2O$—$C_6$–$C_{10}$aryl or $NHCONH_2$;

Z is $CR_{22}$ or N; and $Z_1$ is —$CH_2$—, S, O or $NR_{13}$.

2. A compound of formula I or II according to claim 1, wherein

A is S, or a group of formula A1.

3. A compound of formula I or II according to claim 1, wherein $R_1$ is $OR_9$ or $NR_{10}R_{11}$;

$R_2$, $R_3$, $R_4$ and $R_5$ are independently of each other hydrogen, $C_1$–$C_{12}$alkyl, halogen, $OR_{13}$ or —(CO)$OR_9$;

$R_6$ is $C_1$–$C_{18}$alkylsulfonyl, $C_1$–$C_{10}$haloalkylsulfonyl, camphorylsulfonyl, phenyl-$C_1$–$C_3$alkylsulfonyl, phenylsulfonyl, or naphthylsulfonyl, wherein the groups phenyl and naphthyl, of the radicals phenyl-$C_1$–$C_3$-alkylsulfonyl, phenylsulfonyl and naphthylsulfonyl, are unsubstituted or substituted by one or more halogen, $C_1$–$C_{16}$alkyl and/or $OR_{13}$;

$R'_6$ is phenylenedisulfonyl;

$R_7$ and $R_8$ are independently of one another hydrogen, halogen, $C_1$–$C_6$alkyl, $C_1$–$C_6$alkoxy or $OR_{13}$;

$R_9$ is hydrogen, $C_1$–$C_{18}$alkyl; or phenyl which is unsubstituted or substituted by $C_1$–$C_{18}$alkyl, halogen and/or $C_1$–$C_{12}$alkoxy;

$R_{10}$ and $R_{11}$ independently of one another are hydrogen or $C_1$–$C_{18}$alkyl; or $R_{10}$ and $R_{11}$, together with the nitrogen atom to which they are attached, form a 5-, 6- or 7-membered ring which optionally is interrupted by —O— or by —$NR_{13}$—;

$R_{13}$ is hydrogen, $C_1$–$C_{18}$alkyl or phenyl;

A is S or a group of formula A1

$R_{21}$ and $R_{22}$ independently of each other have one of the meanings given for $R_7$; and Z is $CR_{22}$.

4. A chemically amplified photoresist composition comprising (a) a compound which cures upon the action of an acid or a compound whose solubility is increased upon the action of an acid; and (b) as photosensitive acid donor, at least one compound of the formula I or II according to claim 1.

5. A chemically amplified photoresist composition according to claim 4, which is a positive resist.

6. A chemically amplified positive photoresist composition according to claim 5, comprising (a1) at least one polymer having an acid-labile group which decomposes in the presence of an acid to increase the solubility in aqueous alkaline developer solution; and/or (a2) at least one monomeric or oligomeric dissolution inhibitor having an acid-labile group which decomposes in the presence of an acid to increase the solubility in aqueous alkaline developer solution; and/or (a3) at least one alkali-soluble monomeric, oligomeric or polymeric compound; and (b) as photosensitive acid donor, at least one compound of formula I or II.

7. A chemically amplified photoresist composition according to claim 4, which is a negative resist.

8. A chemically amplified negative photoresist composition according to claim 7, comprising (a4) an alkali-soluble resin as binder;

(a5) a component which, when catalysed by an acid undergoes a crosslinking reaction with itself and/or with the binder; and (b) as photosensitive acid donor, at least one compound of formula I or II.

9. A chemically amplified photoresist composition according to claim 4, in addition to components (a) and (b), comprising further additives (c), further photosensitive acid donor compounds (b1), other photoinitiators (d), and/or sensitizers (e).

10. A process for the preparation of a photoresist by (1) applying to a substrate a photoresist composition according to claim 4;

(2) post apply baking the composition at temperatures between 60° C. and 160° C.;

(3) image-wise irradiating with light of wavelengths between 150 nm and 1500 nm;

(4) optionally post exposure baking the composition at temperatures between 60° C. and 160° C.; and (5) developing with a solvent or with an aqueous alkaline developer.

11. A compound of the formula III

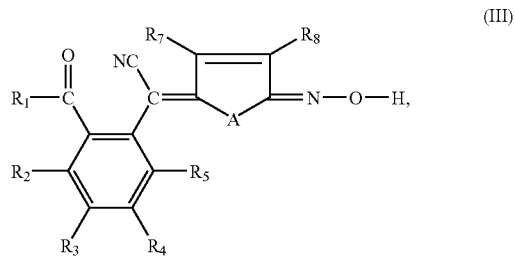

wherein $R_1$, $R_2$, $R_3$, $R_4$, $R_5$, $R_7$, $R_8$ and A are as defined in claim 1.

12. A composition comprising (a) a compound which cures upon the action of an acid or a compound whose solubility is increased upon the action of an acid; and (b) as photosensitive acid donor, at least one compound of the formula I or II according to claim 1.

13. Process for crosslinking compounds that can be crosslinked under the action of an acid, which method comprises adding a compound of formula I and/or II according to claim 1 to the compounds that can be crosslinked and irradiating imagewise or over the whole area with light having a wavelength of 150–1500 nm.

14. Process according to claim 13 for the preparation of surface coatings, printing inks, printing plates, dental compositions, colour filters, resists, image-recording materials, or image-recording materials for recording holographic images.

15. Process according to claim 13 for the preparation of colour filters or chemically amplified resists.

16. Process for the preparation of compounds of the formula I

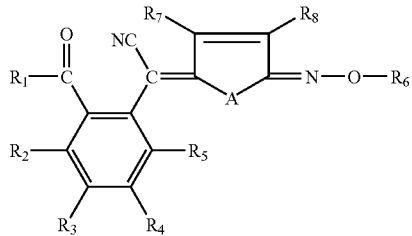

$R_1$, $R_2$, $R_3$, $R_4$, $R_5$, $R_6$, $R_7$, $R_8$ and A are as defined in claim 1, which comprises reacting a compound of formula III

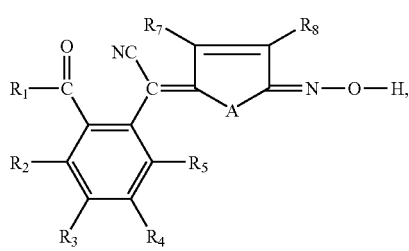

wherein $R_1$, $R_2$, $R_3$, $R_4$, $R_5$, $R_6$, $R_7$, $R_8$ and A are as defined in claim 1, with an acid halide $R_6Cl$ (IV) or acid anhydride $R_6$—O—R (V), comprising the group $R_6$ as defined above; in an inert solvent and in the presence of a base.

17. Process for the preparation of compounds of the formula II

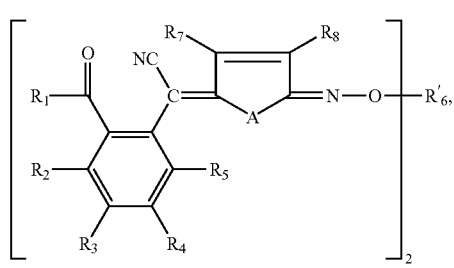

wherein $R_1$, $R_2$, $R_3$, $R_4$, $R_5$, $R_6$, $R_7$, $R_8$ and A are as defined in claim 1, which comprises reacting a compound of formula III

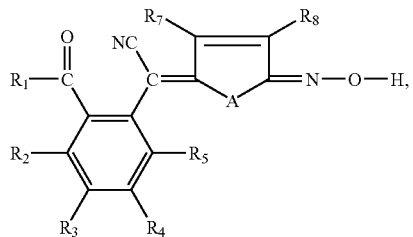

wherein $R_1$, $R_2$, $R_3$, $R_4$, $R_5$, $R_6$, $R_7$, $R_8$ and A are as defined in claim 1, with an acid halide Cl—$R'_6$—Cl (VI), comprising the group $R'_6$ as defined above; in an inert solvent and in the presence of a base.

18. Process for the preparation of compounds of the formula III

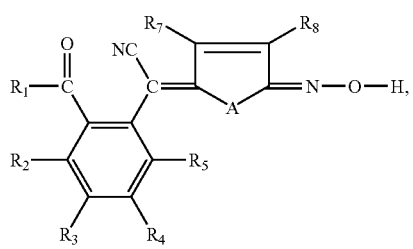

wherein $R_1$, $R_2$, $R_3$, $R_4$, $R_5$, $R_6$, $R_7$, $R_8$ and A are as defined in claim 1, which comprises reacting a compound

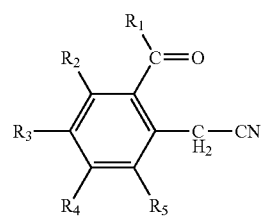

and 2-nitrothiophene, which is substituted by $R_7$ and $R_8$, wherein $R_1$, $R_2$, $R_3$, $R_4$, $R_5$, $R_6$, $R_7$, $R_8$ are as defined above; in a polar solvent and in the presence of a base.

19. Product obtained by reacting 2-nitrothiophene with $R_1$ 2-cyanomethylbenzoate in the presence of a base to give the corresponding free oxime; followed by reaction of said free oxime with a halide $R_6Cl$ or an anhydride $R_6$—O—$R_6$, wherein $R_1$ and $R_6$ are as defined in claim 1, in an inert solvent and in the presence of a base.

* * * * *